US007638151B2

(12) United States Patent
Duan et al.

(10) Patent No.: US 7,638,151 B2
(45) Date of Patent: Dec. 29, 2009

(54) GRAIN COMPOSITIONS CONTAINING PRE-BIOTIC ISOMALTO-OLIGOSACCHARIDES AND METHODS OF MAKING AND USING SAME

(75) Inventors: Gang Duan, Singapore (SG); Feng Li, Wuxi (CN); Jayarama K. Shetty, Pleasanton, CA (US); Julius Vadakoot, Andheri (IN); Sridevi Vadakoot, legal representative, Andheri (IN)

(73) Assignee: Danisco US Inc., Palo Alto, CA (US)

( * ) Notice: Subject to any disclaimer, the term of this patent is extended or adjusted under 35 U.S.C. 154(b) by 756 days.

(21) Appl. No.: 10/798,549

(22) Filed: Mar. 10, 2004

(65) Prior Publication Data

US 2005/0031734 A1 Feb. 10, 2005

Related U.S. Application Data

(60) Provisional application No. 60/477,199, filed on Jun. 9, 2003, provisional application No. 60/453,668, filed on Mar. 10, 2003.

(51) Int. Cl.
*A21D 2/00* (2006.01)
*C12P 19/14* (2006.01)
(52) U.S. Cl. .................. 426/20; 435/101; 435/202; 435/210
(58) Field of Classification Search ................. 435/101, 435/202, 210; 426/20
See application file for complete search history.

(56) References Cited

U.S. PATENT DOCUMENTS

| 3,630,774 | A | * | 12/1971 | Knight | 127/32 |
|---|---|---|---|---|---|
| 3,832,472 | A | * | 8/1974 | Rodgers et al. | 426/627 |
| 3,922,196 | A | | 11/1975 | Leach et al. | 195/31 R |
| 4,113,509 | A | | 9/1978 | Leach et al. | 127/29 |
| 4,575,487 | A | | 3/1986 | Shetty et al. | 435/15 |
| 4,647,538 | A | | 3/1987 | Zeikus et al. | 435/201 |
| 4,970,158 | A | | 11/1990 | Outtrup et al. | 435/201 |
| 4,981,687 | A | | 1/1991 | Fregly et al. | 424/439 |
| 5,096,894 | A | | 3/1992 | Tao et al. | 514/58 |
| 5,141,859 | A | | 8/1992 | Niimi et al. | 435/100 |
| 5,733,579 | A | | 3/1998 | Wolf et al. | 424/606 |
| 5,759,610 | A | | 6/1998 | Nishimoto et al. | 426/658 |
| 5,763,385 | A | | 6/1998 | Bott et al. | 510/392 |
| 5,824,532 | A | | 10/1998 | Barnett et al. | 435/202 |
| 5,958,739 | A | | 9/1999 | Mitchinson et al. | 435/99 |
| 6,008,026 | A | | 12/1999 | Day | 435/96 |
| 6,013,299 | A | | 1/2000 | Haynes et al. | 426/549 |
| 6,025,168 | A | * | 2/2000 | Vercauteren et al. | 435/97 |
| 6,168,821 | B1 | | 1/2001 | Castleberry | 426/590 |
| 6,361,809 | B1 | | 3/2002 | Christophersen et al. | 426/52 |
| 6,492,576 | B2 | | 12/2002 | Kihara et al. | 800/260 |

| 2005/0031734 | A1 | * | 2/2005 | Duan et al. | 426/20 |

FOREIGN PATENT DOCUMENTS

| EP | 0 350 737 A2 | | 1/1990 |
|---|---|---|---|
| EP | 0405283 A2 | * | 1/1991 |
| EP | 0875585 | * | 11/1998 |
| EP | 0 905 256 A1 | | 3/1999 |
| WO | WO 02/20712 A1 | | 3/2002 |

OTHER PUBLICATIONS

International Search Report for PCT/US03/28438 mailed Apr. 27, 2005.
Alexopoulos, C. J., (1962), Introductory Mycology, New York: Wiley.
Benson, Colm P. et al., "Production and Quantification of Transglucosidase from *Aspergillus niger*," *J. Chem. Tech. Biotechnol.*, 32:790-798, 1982.
Bradford, Marion M., "A Rapid and Sensitive Method for the Quantitation of Microgram Quantities of Protein Utilizing the Principle of Protein-Dye Binding," *Analytical Biochemistry*, 72:248-254, 1976.
Faigh, Jilane et al., "Production of Maltose, High Maltose & Very High Maltose Syrups," Technical Bulletin, Genencor International Inc., 2002.
Gibson, Glenn R. et al., "Dietary Modulation of the Human Colonic Microbiota: Introducing the Concept of Prebiotics," *J. Nutr.*, 125:1401-1412, 1994.
Hiromi, Keitaro et al., "Subsite Affinities of Glucoamylase: Examination of the Validity of the Subsite Theory," *Biochimica et Biophysica Acta*, 302:362-375, 1973.
Innis, M. A. et al., "Expression, Glycosylation, and Secretion of an *Aspergillus* Glucoamylase by *Saccharomyces cerevisiae*," *Science*, 228:21-26, 1985.
Kaneko, Toshiyuki et al., "Digestibility of Isomaltooligosaccharides by Rats and Effects on Serum Lipids," *Nippon Nogeikagaku Kaishi*, 66(8):1211-1220, 1992, English abstract only.
Kelly, C. T. et al., "Microbial α-Glucosidases," *Process Biochemistry*, May/Jun., pp. 6-12, 1983.
Kohmoto, Takanobu et al., "Effect of Isomalto-oligosaccharides on Human Fecal Flora," *Bifidobacteria Microflora*, 7(2):61-69, 1988.
Kohmoto, Takanobu et al., "Metabolism of $^{13}$C-Isomaltooligosaccharides in Healthy Men," *Biosci. Biotech. Biochem.*, 56(6):937-940, 1992.

(Continued)

*Primary Examiner*—Chih-Min Kam

(57) ABSTRACT

Methods for the production of substrate, tuber, and grain compositions containing isomalto-oligosaccharides are described. The methods comprise (a) contacting a substrate, tuber or grain containing ungelatinized starch with a maltogenic enzyme and a starch liquefying enzyme to produce maltose; (b) contacting said maltose with a transglucosidic enzyme, wherein said steps (a) and step (b) occur at a temperature less than or at a starch gelatinization temperature; and (c) obtaining a substrate, grain or tuber composition having an enzymatically produced isomalto-oligosaccharide, wherein the oligosaccharide is derived from the grain. The maltogenic enzyme can be either exogenous or endogenous to the grain. The contacting steps can be sequential or concurrent. The present invention also describes flour, oral rehydrating solutions, beer adjuncts, food, feed, beverage additives incorporating the grain compositions made as described.

24 Claims, 2 Drawing Sheets

OTHER PUBLICATIONS

Manjunath, P. et al., "Fungal Glucoamylases," *Journal of Applied Biochemistry*, 5: 235-260, 1983.

McCleary, Barry V. et al., "Purification, Properties, and Industrial Significance of Transglucosidase from *Aspergillus niger*," *Carbohydrate Research*, 185:147-162, 1989.

Meagher, Michael, et al., "Subsite Mapping of *Aspergillus niger* Glucoamylases I and II with Malto- and Isomaltooligosaccharides," *Biotechnology and Bioengineering*, 34:681-688, 1989.

Modler, H. W., "Compounds Which Enhance the Growth of Probiotic Bacteria," presented at the International Roundtable on Animal Feed Biotechnology, Ottawa, Ontario, Canada, 1992.

Ooshima, Takashi et al., "The Caries Inhibitory Effects of GOS-Sugar in vitro and in Rat Experiments," *Microbiol. Immunol.*, 32(11):1093-1105, 1988.

Park, Jong-Hyun et al., "Growth Effect of Branched Oligosaccharides on Principal Intestinal Bacteria," *Kor. J. Appl. Microbiol. Biotechnol.*, 20(3):237-242, 1992, English abstract only.

Pazur, John H., et al., "The Hydrolysis of $\alpha$-D-Glucosides by Amyloglucosidase from *Aspergillus niger*," *The Journal of Biological Chemistry*, 237(4):1002-1006, 1962.

Pazur, John H. et al., "The Synthesis of 1,6-Anhydro-$\beta$-D-Glucopyranose and D-Glucosyl Oligosaccharides From Maltose by a Fungal Glucosyltransferase," *Carbohydrate Research*, 61:279-290, 1978.

Shetty, J. K. at al., Transglucosylation of Malto-oligosaccharides. Paper presented at 50$^{th}$ Starch Convention, Detmold, Germany. Apr. 21-23, 1999 see first page attached.

Suzuki, Yuzuru et al., "Assignment of a $\alpha$-Nitrophenyl $\alpha$-D-Glucopyranosidase of *Bacillus stearothermophilus* ATCC 12016 to a Novel Exo-$\alpha$-1,4-Glucosidase Active for Oligomaltosaccharides and $\alpha$-Glucans," *Biochimica et Blophysica Acta*, 787:281-289, 1984.

Swinkels, J. J. M., "Sources of Starch, Its Chemistry and Physics," Starch Conversion Technology (Marcel Dekker, Inc., New York, New York, pp. 15-46 (1985).

Tomasik, Prezemyslaw Jan et al., "Probiotics and Prebiotics," *Cereal Chem.*, 80(2):113-117, 2003.

Lu et al., "Study on preparation of isomalto-oligosacchardes from wheat starch," J. of Zhenzhou Institute of Technology, V. 22/2 (Jun. 2001) pp. 1-7.

Translation of Enzymatic Formulation Practical Technology Handbook, edited by XiRui Jiang, pp. 21-49, Mar. of 2002.

* cited by examiner

PROCESS FOR
PRODUCING GRAIN/TUBER COMPOSITION
CONTAINING ISOMALTO-ISOMALTO-OLIGOSACCHARIDES

Example: Grain/Tuber

PROCESS FOR PRODUCING GRAIN COMPOSITION CONTAINING ISOMALTO-OLIGOSACCHARIDES
Example: Wheat

GRAIN COMPOSITIONS CONTAINING PRE-BIOTIC ISOMALTO-OLIGOSACCHARIDES AND METHODS OF MAKING AND USING SAME

RELATED APPLICATIONS

This application claims priority to U.S. Provisional Application No. 60/477,199, filed Jun. 9, 2003, and U.S. Provisional Application No. 60/453,668, filed Mar. 10, 2003.

TECHNICAL FIELD

The present invention describes grain compositions containing isomalto-oligosaccharides and methods for making the same. The method includes the derivation of the isomalto-oligosaccharides from the starch contained within the grain.

BACKGROUND OF THE INVENTION

Isomalto-oligosaccharides ("IMOs") are mixed linkage oligosaccharides, having mixtures of 1,4 alpha and/or 1,6 alpha glucosidic linkages. They are also known as anomalously linked oligosaccharides ("ALOs"). Isomalto-oligosaccharides contain a substantial amount of branched oligosaccharides such as isomaltose, panose, isomaltotriose, isomaltotetraose, isopanose and higher branched oligo-saccharides.

There is a market demand for products containing IMO's. IMO products are sold in powder or liquid form, depending on the intended application. The potential applications are situated in the food area. Examples of IMO products are: seasonings (mayonnaise, vinegar, soup base etc.), confectionery (candy, chewing gum, chocolate, ice cream, sherbet, syrup), processed foods of fruits and vegetables (jam, marmalade, fruit sauces, pickles), meat or fish foods (ham, sausage, etc.), bakery products (bread, cake, cookie, pastry), precooked foods (salad, boiled beans, etc.), canned and bottled foods, convenience foods (instant coffee, instant cake base, etc.), and beverages, both alcoholic (liquor, seju, wine, sake, beer [International Publication No. WO 02/20712 A1], etc.) and non-alcoholic (coffee, juice, nectar, aerated or carbonated drinks, lemonade, cola). Isomalto-oligosaccharide can further be applied as ingredients in animal feed and pet foods. Non-food application areas are cosmetics and medicine (cigarette, lipstick, toothpaste, internal medicine, etc.).

Isomalto-oligosaccharides belong to a group of oligosaccharides classified as functional-health food oligosaccharides ("FHFO"). Exemplary IMO's include fructo-oligosaccharides, galacto-oligosaccharides, xylo-oligosaccharides and gentio-oligosaccharides. IMO's have been linked to the increase of the general well being of humans and animals when taken orally on a regular daily basis and are classified as "prebiotics". Prebiotics are defined as non-digestible substances (e.g., dietary fiber) that exert some biological effect on humans by selective stimulation of growth or bioactivity of beneficial microorganisms either present or therapeutically introduced to the intestine. (Przemyslaw Jan Tomasik and Piotr Tomasik. 2003 American Association of Cereal Chemists, Inc. 80(2): 113-117). The "prebiotic" action of the oligosaccharides is to increase the numbers of *bifidobacteria* and *lactobacilli* ("prebiotic") in the large intestine and to reduce the concentration of putrifactive bacteria. *Bifidobacteria* are associated with some health promoting properties like the inhibition of the growth of pathogens, either by acid formation or by anti-microbial activity. They are also associated with such diverse effects as the modulation of the immune system (anti-tumor properties), the reduction of the levels of triglycerides and cholesterol, the production of vitamins (B group), the reduction of blood ammonia concentrations, the prevention of translocation, the restoration of the normal gut flora after anti-microbial therapy, the production of digestive enzymes, the reduction of antibiotic associated side effects (Kohmoto T., Fukui F., Takaku H., Machida Y., et al., *Bifidobacteria* Microflora, 7(2)(1988),61-69; Kohmoto K., Tsuji K., Kaneko T., Shiota M., et al., Biosc. Biotech. Biochem., 56(6)(1992),937-940; Kaneko T., Kohmoto T., Kikuchi H., Fukui F., et al., Nippon Nogeikagaku Kaishi, 66(8)(1992),1211-1220, Park J-H, Jin-Young Y., Ok-Ho S., Hyun-Kyung S., et al., Kor. J. Appl. Microbiol. Biotechnol., 20(3)(1992), 237-242). Modler, H. W., 1992, "Compounds which enhance the growth of Prebiotic Bacteria", presented at the International Roundtable on Animal Feed Biotechnology, Ottawa, Ontario, Canada.

The isomalto-oligosaccharides are synthesized by an enzyme catalyzed transglucosylation reaction using a D-glucosyltransferase (E.C. 2.4.1.24, transglucosidase, alpha-glucosidase). This enzyme catalyzes both hydrolytic and transfer reactions on incubation with alpha-D-gluco-oligosaccharides. The transfer occurs most frequently to 6-OH (hydroxyl group 6 of the glucose molecule), producing isomaltose from D-glucose, or panose from maltose. The enzyme can also transfer to the 2-OH or 3-OH of D-glucose to form kojibiose or nigerose, or back to 4-OH to reform maltose. As a result of transglucosidase reactions, the malto-oligosaccharides are converted into isomalto-oligosaccharides resulting in a class of oligosaccharides containing a higher proportion of glucose moieties linked to a primary hydroxyl group of a glucose molecule from the non-reducing end, e.g., by alpha-D-1,6 glucosidic linkages. The transglucosidase from *A. niger* acts only on oligosaccharides with a low degree polymerization (DP) (McCleary B. V., Gibson T. S., Carbohydrate Research 185(1989)147-162; Benson C. P., Kelly C. T., Fogarty W. M., J. Chem. Tech. Biotechnol., 32(1982)790-798; Pazur J. H., Tominaga Y., DeBrosse C. W., Jackman L. M., Carbohydrate Research, 61(1978) 279-290). Degree of polymerization refers to the number of dextrose units. For example, a diglucosyl molecule, for example maltose, has a DP of 2. These sugars are receiving increased attention as food additives because they help prevent dental caries (Oshima, et. al 1988. The caries inhibitory effects of gos-sugar in vitro and rat experiments. Microbial Immunol. 32, 1093-1105) and improve human intestinal microflora acting as a growth factor (prebiotic) for *bifidobacteria* (Komoto, et. al 1988; Effect of Isomalto-oligosaccharides on human fecal flora *Bifidobacteria* Micro flora 7, 61-69).

Isomalto-oligosaccharides can be obtained in different ways. For example glucose syrups at high dry solids concentration i.e. 60-80% are treated with glucoamylase resulting in the formation of isomalto-oligosaccharides mainly DP2. The high solids levels are present to force the reaction to reverse from the normal direction in favor of hydrolysis.

Grains, including wheat, barley, etc., are excellent raw materials in the commercial production of many value added functional food ingredients such as wheat flour, starch, starch hydrolysates (glucose, fructose, high maltose syrup, etc.) and wheat gluten. Syrup containing a high level of maltose is also used in many microbial fermentations as a carbon source in the production of antibiotics, pharmaceuticals, vaccines, biochemical, such as alcohol (both potable and fuel), amino acids, organic acids, etc and recently in the production of functional health-food oligosaccharides called isomalto-oligosaccharides. In a conventional process for the production of starch hydrolysate, such as maltose syrups, the insoluble granular starch is generally separated from other cellular components of wheat prior to the hydrolysis by starch liquefying and maltogenic alpha amylases enzymes. Maltose is a disaccharide consisting of two glucosyl residues linked by α 1-4 D-glucosidic linkage and is the smallest in the family of malto-oligosaccharides. It is produced on a large scale as syrup, powder and crystals in several grades of purity. Various maltose syrups are drawing considerable interest for commercial applications in brewing, baking, soft drink canning, confectionary and other food and beverage industries. Ultra pure maltose is used as an intravenous nutrient in Japan. Catalytic reduction of maltose results in maltitol, which is considered to be a low calorie sweetener. Recently, high maltose syrup has become a key raw material for industrial production of isomalto-oligosaccharides (J. K. Shetty and O. J. Lantero, 1999 "Transglucosylation of Malto-oligosaccharides." Paper presented at 50th Starch Convention, Detmold, Germany).

In a conventional process for the production of starch hydrolysate such as high maltose syrup, the insoluble starch is separated prior to the hydrolysis by thermostable liquefying alpha amylases [EC 3.2.1.2,alpha (1,4)-glucan glucanohydrolase] derived either from *Bacillus licheniformis* or *Bacillus stearothermophilus*. Hydrolysis of the purified starch (refined) is carried out by suspending insoluble granular starch in water (30-35% dissolved solid basis [dsb]) and heated to a temperature of between 85° C. and 120° C. to solubilize the starch and making it susceptible for enzymatic hydrolysis. The liquefied starch is further processed to manufacture starch hydrolysate with different carbohydrate composition using specific maltose producing enzymes such as fungal alpha amylase (sold under the tradename CLARASE L from Genencor International, Palo Alto, Calif.) for syrup containing less than 55% maltose, β Amylase (sold under the tradename OPTIMALT BBA from Genencor International, Palo Alto, Calif.) for syrup containing maltose content between 55% and 62% and less than 1% glucose. For higher levels of maltose syrup, >62%, addition of debranching enzyme (sold under the tradename OPTIMAX L-1000 from Genencor International, Palo Alto, Calif.) in conjunction β Amylase is useful. (Faigh, J.; Duan, G.; Strohm, B. and Shetty, J. (2002) "Production of Maltose, High Maltose & Very High Maltose Syrups," Technical Bulletin, Genencor International Inc.).

A process for converting granular starch (refined) into soluble hydrolysate by incubating with bacterial alpha amylase at a temperature below the starch gelatinization temperature (Leach et. al 1978; U.S. Pat. No. 4,113,509) and subsequent hydrolysis by beta amylase to produce high maltose syrup have been reported (Leach et. al 1975; U.S. Pat. No. 3,922,196), However the syrup produced by such process resulted in only 55% maltose of the total sugar content, with a very high level of maltotriose. The process for producing high maltose syrup using liquefied starch (gelatinized followed by hydrolysis using thermostable alpha amylase) is described in European Patent Application #0905256 (Christophersen, et. al 2000) and U.S. Pat. No. 5,141,859 (Nimmi, et. al 1992). The process is cumbersome, expensive and it requires the separation of starch from other cellular components, high cost of the additional maltose producing enzymes, high temperature treatment and longer reaction time. European Patent Application #0350737 A2 (Shinke, et. al 1989) disclosed a process for producing maltose syrup by hydrolyzing a granular (purified) starch from corn, wheat, potato and sweet potato at 60° C. without the conventional liquefaction step (gelatinization followed by liquefaction at high temperature) using an alpha amylase from *Bacillus stearothermophilus*. However, the hydrolyzed starch resulted in a maltose concentration ranging from 50% to 55%. The syrup also contained very high level of maltotriose (30-36%). The process resulted in a ratio of maltose to maltotriose less than 2.0 irrespective of the source of the starch. Maltose syrup containing a high level of maltotriose is not a preferred substrate as carbon feed in many microbial fermentations including the alcohol fermentation by yeast because of the difficulties in metabolizing maltotriose. Maltose is a preferred donor of glucosyl residue in the transglucosylation reaction catalyzed by glucosyltransferases in the production of isomalto-oligosaccharides (J. K. Shetty and O. J. Lantero, 1999 "Transglucosylation of Malto-oligosaccharides." Paper presented at 50th Starch Convention, Detmold, Germany). U.S. Pat. No. 6,361,809 described a method for producing maltose and a limit dextrin by treating the purified granular waxy maize starch with a hydrolase, maltogenase alpha amylase classified as EC 3.2.1.133 from *Bacillus stearothermophilus* followed by separating the maltose using ultra filtration process. Evaporation of the dilute permeate containing the maltose is expensive because of high energy cost and also faces a very high risk of microbial contamination.

Traditionally grains such as wheat, malt, sorghum (milo), millet (ragi), particularly whole grains are used in nutrition as carriers of macro- and micro-elements, proteins, fiber and vitamins. The majority of cereal grains appeared to be too readily digested to play an effective role as prebiotics or even as nutraceuticals. It has been suggested that designing genetically modified, less digestible cereals suitable as prebiotics to manipulate gut microflora (Gibson, G. R, and Roberfroid, M. B. 1995, Dietary modulation of the human colonic microflora: Introducing the concept of prebiotics. J. Nutr. 125, 1401-1412).

There is a continuing interest in methods for producing grain compositions with isomalto-oligosaccharides enzymatically derived from the source substrate, e.g., grain or tuber, without having to separate the starch from other grain components and/or subject the starch of the substrate to high temperatures of jet cooking prior to transglucosidation action. There is also a continuing interest in low pH processes for minimizing the risk of microbial contamination. The present invention addresses these interests.

SUMMARY OF THE INVENTION

The present invention describes a method for making an isomalto-oligosaccharide grain composition said method comprising: (a) contacting a ungelatinized starch containing grain with a maltogenic enzyme and a starch liquefying enzyme to produce maltose; (b) contacting said maltose with a transglucosidic enzyme, wherein said steps (a) and step (b) occur at a temperature less than or at a starch gelatinization temperature; and (c) obtaining a grain composition having an enzymatically produced isomalto oligosaccharide, wherein said oligosaccharide is derived from said grain.

Optionally, in one embodiment, the steps (a) and (b) occur concurrently. In another embodiment, the method further includes a step of drying said grain composition. In another embodiment the grain is selected from the group consisting of wheat, rye, barley, malt and rice. In another embodiment the grain is selected from the group consisting of sorghum, millet and rice. In another embodiment, the maltogenic enzyme is a beta amylase. In another embodiment, the maltogenic enzyme is endogenous to said grain. In another embodiment, the maltogenic enzyme is exogenous to said grain. In another embodiment, the starch liquefying enzyme is an alpha amylase derived from a *Bacillus*. In another embodiment, the starch liquefying enzyme is derived from *Bacillus lichenifor-*

*mis* or *Bacillus stearothermophilus*. In another embodiment, the transglucosidic enzyme is a transglucosidase. In another embodiment, the transglucosidase is derived from *Aspergillus*. In another embodiment, the transglucosidase derived from *Aspergillus niger*. Another embodiment of the present invention includes a grain composition produced according to above described method. Another embodiment of the present invention includes a food additive comprising said grain composition described above.

The present invention also describes a method for making an isomalto-oligosaccharides enriched flours at temperatures at or below the gelatinization temperature wherein an ungelatinized grain having an endogenous maltogenic enzyme are contacted with a solubilizing enzyme selected from *Bacillus* to produce a maltose syrup. The maltose syrup is contacted with a transglucosidase to produce a substrate (tuber or grain) composition including isomalto-saccharides derived therefrom.

The present invention also describes a method for making an isomalto-oligosaccharides enriched flours at temperatures at or below the gelatinization temperature wherein an ungelatinized grain having an endogenous maltogenic enzyme (wheat, barley, etc.) are mixed with ungelatinized grain not having endogenous maltogenic enzymes (e.g., sorghum, miller or rice), the grain mixture being contacted with a solubilizing enzyme selected from *Bacillus* to produce a maltose syrup. The maltose syrup is contacted with a transglucosidase to produce a substrate (tuber or grain) composition including isomalto-saccharides derived therefrom.

The present invention also describes a method for making a wheat grain composition said method comprising: (a) contacting an ungelatinized wheat grain having an endogenous maltogenic beta-amylase and a starch liquefying alpha amylase from *Bacillus* to produce maltose; (b) contacting said maltose with a transglucosidase, wherein said steps (a) and step (b) occur at a temperature less than wheat gelatinizing temperature; and (c) obtaining a wheat grain composition having an enzymatically produced isomalto-oligosaccharide, wherein said oligosaccharide is derived from said ungelatinized grain.

Optionally, in another embodiment the method uses the above method for making a grain composition for making a food additive. Another embodiment includes a grain composition made accordingly. Another embodiment includes a flour comprising the grain composition described above. Another embodiment includes an isomalto-saccharide made according to the method described above. Another embodiment includes an oral rehydration solution comprising the isomalto-oligosaccharide above. Another embodiment includes a grain composition comprising an ungelatinized grain and at least one isomalto-oligosaccharide, wherein said isomalto-oligosaccharide is enzymatically derived from said ungelatinized grain. In another embodiment the grain composition contains greater than 1% by weight of at least one isomalto-oligosaccharide.

DETAILED DESCRIPTION OF THE INVENTION

Definitions

Figure 1:
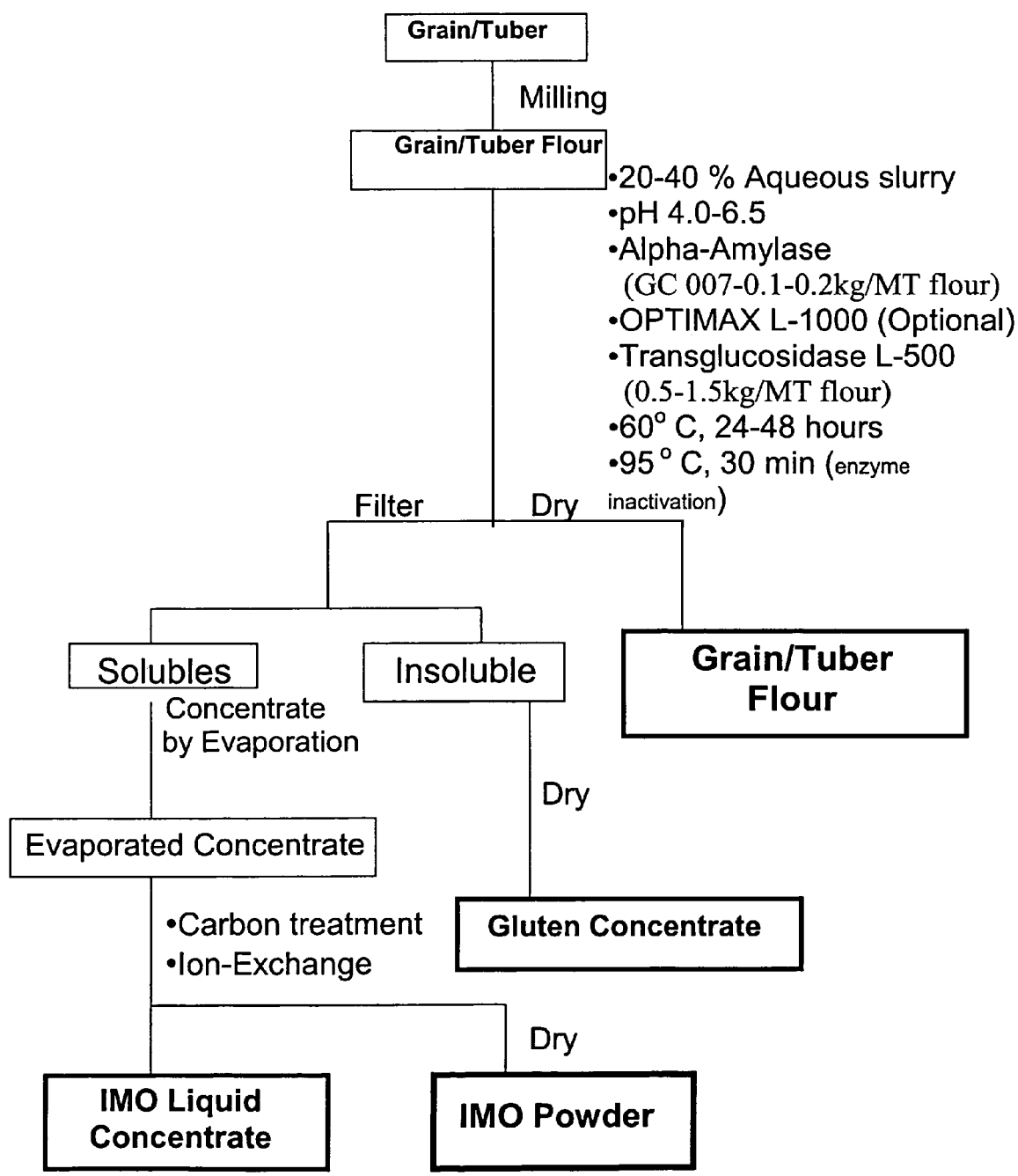
FIG. 1 is a flowchart describing the production of isomalto-oligosaccharide enriched flour.

The term "grain" refers to a plant, which is classified as a cereal or as a monocotyledonous plant belonging to the Poales order, in particular the family Poaceae. Examples of plants belonging thereof are plants selected from the genuses *Triticum* (wheat), *Hordeum* (barley); *Secale* (rye); *Zea* (corn or maize); *Avena* (oats), *Fagopryum* (buckwheat); *Sorghum* (sorghum or milo), *Panicum* or *Setaria* (millet or ragi); or *Oryza* (rice).

For example, in one embodiment, the term "wheat" refers to a plant which is classified or once was classified as a strain of *Triticum aestivum*.

For example, in one embodiment, the term "barley" refers to a plant which is classified or once was classified as a strain of *Hordeum vulgare*.

For example, in one embodiment, the term "rye" refers to a plant, which is classified or once was classified as a strain of *Secale cereale*.

For example, in one embodiment, the term "corn" refers to a plant, which is classified or once was classified as a strain of *Zea mays*.

For example, in one embodiment, the term "oats" refers to a plant, which is classified or once was classified as a strain of *Avena sativa*.

For example, in one embodiment, the term "buckwheat" refers to a plant, which is classified or once was classified as a strain of *Fagopryum esculentum*.

For example, in one embodiment, the term "sorghum" refers to a plant, which is classified or once was classified as a strain of *Sorghum bicolor*.

For example, in one embodiment, the term "millet" refers to a plant, which is classified or once was classified as a strain of *Panicum miliaceum* or *Setaria italica*.

For example, in one embodiment, the term "rice" refers to a plant which is classified or once was classified as a strain of *Oryza sativa*.

The term tuber refers to a starchy storage organ (for example a potato, sweet potato, yam, manioc, etc) formed by swelling of an underground stem or the distal end of a root.

For example, in one embodiment, the term "potato" refers to a plant which is classified or once was classified as a strain of *Solanum tuberosum*.

For example, in one embodiment, the term "sweet potato" refers to a plant which is classified or once was classified as a strain of *Ipom[oe]a balatas*.

For example, in one embodiment, the term "yam" refers to a plant which is classified or once was classified as a strain of *Dioscorea sativa, D. villosa, C. batatas*.

The term substrate refers to materials that can be enzymatically converted to maltose and thus IMO's. The term "substrate" includes, for example, grains and tubers. Furthermore, the term substrate includes all forms of the grain (polished or unpolished) or tuber, such as whole grains, broken grains, grits and flour and any plant part.

The term "starch" refers to any material comprised of the complex polysaccharide carbohydrates of plants, comprised of amylose and amylopectin with the formula $(C_6H_{10}O_5)_x$, wherein X can be any number.

The term "granular starch" refers to uncooked (raw) starch, which has not been subject to gelatinization. The term "gelatinization" refers to solubilization of a starch molecule to form a viscous suspension.

The phrases "substrate", "grain" or "tuber" containing ungelatinized starch" refer to an ungelatinized substrate, grain or tuber that is not subjected to temperatures greater than the starch gelatinization temperatures which result in effecting a gelatinization or liquefaction of the starch contained within the substrate.

The term "maltose" refers to a disaccharide having two glucosyl residues linked by an alpha 1-4 D-glucosidic linkage The term "isomaltose" refers to a disaccharide having two glucosyl residues linked by an alpha 1,6 D-glucosidic linkage.

The term "isomalto-oligosaccharide" (IMO) refers to sugars having at least two glucosyl residues linked by alpha 1,6 glucosidic linkages at the non-reducing end. In addition term refers to anomalously linked oligosaccharides, saccharides having both alpha 1,6 and alpha 1,4 glucosidic linkages. Exemplary isomalto-oligosaccharides include isomaltose, panose, and isomalto-triose The term "isomalto-oligosaccharide" grain composition refers to grain compositions characterized by isomalto-sugars level of at least 1% (w/w %) of the total sugar content as determined by high performance liquid chromatographic methods.

The term "maltogenic enzyme" refers to an enzyme that converts starch to maltose. Exemplary maltogenic enzymes include fungal, bacterial and plant derived alpha amylases and beta-amylases.

The term "amylases" refers to enzymes that catalyze the hydrolysis of starches.

The term "alpha-amylase" refers to enzymes of the class (E.C.) 3.2.1.1 and/or 3.2.1.133 that catalyze the hydrolysis of alpha-1,4-glucosidic linkages. These enzymes have also been described as those effecting the exo or endohydrolysis of 1,4-alpha-D-glucosidic linkages in polysaccharides containing 1,4-alpha-linked D-glucose units. Another term used to describe these enzymes is glycogenase. Exemplary enzymes include alpha-1,4-glucan 4-glucanohydrase glucanohydrolase.

The term "beta-amylase" refers to enzymes of the class (E.C.) 3.2.1.2 that catalyze the hydrolysis of alpha-1,4 glucosidic linkages releasing maltose units. These enzymes have also been described as those effecting the hydrolysis of 1,4-alpha-D-glucosidic linkages in polysaccharides so as to remove successive maltose units from the non-reducing end of chains.

The term "transglucosidic" enzyme refers to an enzyme that catalyzes both hydrolytic and transfer reactions in incubation with alpha D-gluco-oligosaccharides. Exemplary enzymes include transglucosidases and/or those of the class (E.C.) 2.4.1.24, e.g., D-glucosyltransferase. These enzymes have also been referred to as 1,4-alpha-glucan 6-alpha-glucosyltransferase and oligoglucan-branching glycosyltransferase.

The term debranching enzyme refers to enzymes that catalyze the hydrolysis of alpha-1,6-linkages. An enzyme of the class E.C. 3.2.1.41 is useful in this regard. An exemplary enzyme of this class is a pullanase, also known as alpha-dextrin endo-1,6-alpha glucosidase, limit dextrinase, debranching enzyme, amylopectin 1,6-glucanohydrolase. Additional exemplary enzymes of the class (E.C.) 3.2.1.41, e.g., pullulanases, [alpha-(1-6)-glucan 6-glucanohydrolase, also called alpha-(1,6)-glucosidase]).

The term "starch gelatinizing temperatures" refers to a temperature sufficiently high to effect liquefying or gelatinization of granular starch. Heating a starch in water causes the starch granules to swell. At sufficient solids concentration, the swollen granules occupy most of the space and a viscous mass, called a paste, results. Solubilization of starch molecule is called gelatinization. Gelatinization is accompanied by a loss of birefringence. The term starch gelatinizing temperature refers to the temperature at which gelatinization occurs.

The term "starch liquefying enzyme" refers to an enzyme that effects the fluidization of granular starch. Exemplary starch liquefying enzymes include alpha amylases of the class (E.C.) 3.2.1.1.

The term "endogenous" refers to the enzyme being present in the grain or tuber without having to resort to adding the maltogenic enzyme to the grain.

The term "exogenous" enzyme refers to an enzyme that is not present within the grain. Exemplary exogenous enzymes include, for example, maltogenic enzymes not present in the wild-type substrate, e.g., rice, millet, etc.

The term "total sugar content" refers to the total amount of sugar present in a starch, grain or tuber composition.

The term "IMO No." is calculated as the sum of isomaltose, panaose, isomaltotriose and branched sugars greater than DP3. The IMO Number provides an indication of the amount of IMO compounds present in the compound or solution.

The term "ratio of branched sugars" ("RBS") refers to the ratio of maltose (DP2) present in the grain as compared to the level of maltotriose (DP3) present in the resultant grain composition.

The term "Degrees of Diastatic Power" (DP°) unit refers to the amount of enzyme contained in 0.10 ml of a 5% solution of the sample enzyme preparation that will produce sufficient reducing sugars to reduce 5 ml of Fehling's solution when the sample is incubated with 100 ml of substrate for 1 hour at 20° C. (68° F.).

The term "DE" or "dextrose equivalent" is an industry standard for measuring the concentration of total reducing sugars, calculated as D-glucose on a dry weight basis. Unhydrolyzed granular starch has a DE that is essentially 0 and D-glucose has a DE of 100.

The term "total sugar content" refers to the total sugar content present in a starch composition.

The terms "dry solid basis" and "dsb" refer to the total amount of compound, e.g., flour, of a slurry (in %) on a dry weight basis.

The terms "dry solid content", "dry solid granular starch", "dry solid starch" and "(dss)" refer to the total starch of a slurry (in %) on a dry weight basis.

The term "Brix" refers to a well known hydrometer scale for measuring the sugar content of a solution at a given temperature. Thus the term "Brix" refers to a measure of the solubilized sugars in solution. The Brix scale measures the number of grams of sucrose present per 100 grams of aqueous sugar solution (the total solubilized solid content). For example, a measurement of 1.00 Brix refers to about 10 mg/ml of sugar in solution. Brix measurements are frequently made by use of a hydrometer or refractometer.

The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A "DP4+" denotes polymers with a degree of polymerization of greater than 3.

The term "enzymatically produced" refers to enzymatic catalysis of the substrate to the IMO as opposed to chemical or organic chemical synthesis of the IMO. The term "filamentous fungi" refers to all filamentous forms of the subdivision Eumycotina (See, Alexopoulos, C. J. (1962), INTRODUCTORY MYCOLOGY, New York: Wiley). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic. In the present invention, the filamentous fungal parent cell may be a cell of a species of, but not limited to, *Trichoderma*, e.g., *Trichoderma reesei* (previously classified as *T. longibrachiatum* and currently also known as *Hypocrea jecorina*), *Tricho-*

*derma viride, Trichoderma koningii, Trichoderma harzianum; Penicillium* sp.; *Humicola* sp., including *Humicola insolens* and *Humicola grisea; Chrysosporium* sp., including *C. lucknowense; Gliocladium* sp.; *Aspergillus* sp., including *A. oryzae, A. nidulans, A. niger*, and *A. awamori; Fusarium* sp., *Neurospora* sp., *Hypocrea* sp., and *Emericella* sp. Reference is also made to Innis et al., (1985)

Sci. 228:21-26.

The term "*Aspergillus*" or "*Aspergillus* sp." refers to any fungal strain, which had previously been classified as *Asperilglus* or is currently classified as *Aspergillus*.

The term "bacterial" refers to *Bacillus* species of, but not limited to *B. subtilis, B. amyloliquefaciesn, B. lentus, B. Carlsberg, B. licheniformis*, and *B. stearothermophilus*

The term "plant origin" refers to the enzyme being derived, extracted, isolated, expressed from a plant source, for example from barley malt, soybean, wheat or barley.

The term "contacting" refers to the placing of the respective enzyme[s] in sufficiently close proximity to the respective substrate to enable the enzyme[s] to convert the substrate to the desired end-product. Those skilled in the art will recognize that mixing solutions of the enzyme or enzymes with the respective substrates can effect contacting.

The term "incubating" refers to mixing a substrate containing substrate with the respective enzymes, e.g., liquefying or maltogenic or transglucosidase under given conditions for a defined period of time.

The term "enzymatic conversion" refers to the modification of a rice substrate to yield soluble hydrolyzed granular rice starch and preferably to yield glucose.

The term "slurry" refers to an aqueous mixture containing insoluble granular starch. Sometimes the terms "slurry" and "suspension" are used interchangeably herein.

The term "culturing" refers to growing a population of microbial cells under suitable conditions in a liquid or solid medium. In one embodiment, culturing refers to fermentative bioconversion of a granular starch substrate to glucose syrup or other desired end products (typically in a vessel or reactor). For example, in one embodiment, the term alpha amylase enzyme unit is defined as the amount of alpha amylase which hydrolyzes 1 micromole of starch substrate in 1 min under standard assay conditions of pH 5.2 and 40° C. For example, in one embodiment, the term beta amylase enzyme unit is defined as the amount of beta amylase which hydrolyzes 1 micromole of starch substrate in 1 min under standard assay conditions of pH 4.6 and 20° C.

For example, in one embodiment, the term transglucosidase unit is defined as the amount of transglucosidase which converts 1 micromole of maltose substrate in 1 min under standard assay conditions of pH 4.8 and 37° C. In another embodiment, the term transglucosidase unit is defined as the amount of transglucosidase which produces 1 micromole of panose per minute under standard assay conditions of pH 4.8 and 37° C.

For example, in one embodiment, the term one Liquefon Unit (LU) is the measure of digestion time required to produce a color change with iodine solution, indicating a definite stage of dextrinization of starch substrate under standard assay conditions of pH 5.6 and 25° C.

"ATCC" refers to American Type Culture Collection located at Manassas, Va. 20108 (ATCC, refer to the website for atcc.org).

"NRRL" refers to the Agricultural Research Service Culture Collection, National Center for Agricultural Utilization Research (and previously known as USDA Northern Regional Research Laboratory), Peoria, Ill.

"NCBI" refers to the National Center for Biotechnology Information, Natl Library Med. (refer to the website for NCBI at the National institutes of Health ncbi.nlm.nih.gov/).

"A", "an" and "the" include plural references unless the context clearly dictates otherwise.

The present invention describes a method for making an isomalto-oligosaccharide substrate, grain or tuber composition said method comprising: (a) contacting a ungelatinized starch containing substrate, e.g., a grain or a tuber, with a maltogenic enzyme and a starch liquefying enzyme to produce maltose; (b) contacting said maltose with a transglucosidic enzyme, wherein said steps (a) and step (b) occur at a temperature less than or at a starch gelatinization temperature; and (c) obtaining a substrate, grain or tuber composition having an enzymatically produced isomalto-oligosaccharide, wherein said oligosaccharide is derived from said substrate, grain or tuber. An embodiment of the present invention is depicted in FIG. 1.

The present invention also describes a method for making an isomalto-oligosaccharide-enriched substrate, grain or tuber compositions, flours, oral rehydrating solutions, and/or food additives, at temperatures at or below the gelatinization temperature wherein a substrate having or containing an ungelatinized starch and having endogenous maltogenic enzyme are contacted with a solubilizing enzyme selected from *Bacillus* to produce a maltose syrup. The maltose syrup is then contacted with a transglucosidase at a temperature at or less than gelatinization or liquefaction temperatures to produce a grain composition having isomalto-oligosaccharides. In one embodiment, the grain composition is characterized by a sugar composition of greater than 60% maltose and a ratio of branched sugars of greater than 2.0 to 1.0. The conversion of the substrate to the IMO can be enzymatically produced.

The present invention also describes a method for making an isomalto-oligosaccharide substrate, grain or tuber composition, the method comprising: (a) contacting a substrate, grain or tuber containing a starch with a maltogenic enzyme and a starch liquefying enzyme to produce a maltose; (b) contacting the maltose with a transglucosidic enzyme, wherein the steps (a) and step (b) occur at a temperature less than or at starch gelatinization temperature; and (c) obtaining a substrate, grain or tuber composition having an enzymatically produced isomalto-oligosaccharide, wherein the oligosaccharide is derived from the substrate, grain or tuber. The invention optionally further describes an additional step of separating soluble constituents from insoluble constituents. The invention further describes an additional step of drying the substrate, grain or tuber composition. In one embodiment the grain is selected from the group consisting of wheat, rye, barley, malt, buckwheat, sorghum (milo), millet (ragi) and rice. In another embodiment, the maltogenic enzyme is a beta amylase. In another embodiment, the maltogenic enzyme is endogenous to the grain. In another embodiment, the starch liquefying enzyme is an alpha amylase derived from a *Bacillus*. In another embodiment, the starch liquefying enzyme is derived from *Bacillus licheniformis* or *Bacillus stearothermophilus*. In another embodiment, the transglucosidic enzyme is a transglucosidase. In another embodiment. The transglucosidase is derived from *Aspergillus*. In another embodiment, the *Aspergillus* is *Aspergillus niger*. The invention also describes a grain composition, a food additive, oral rehydration solution, food product and/or a flour produced according to above described method.

Figure 2:
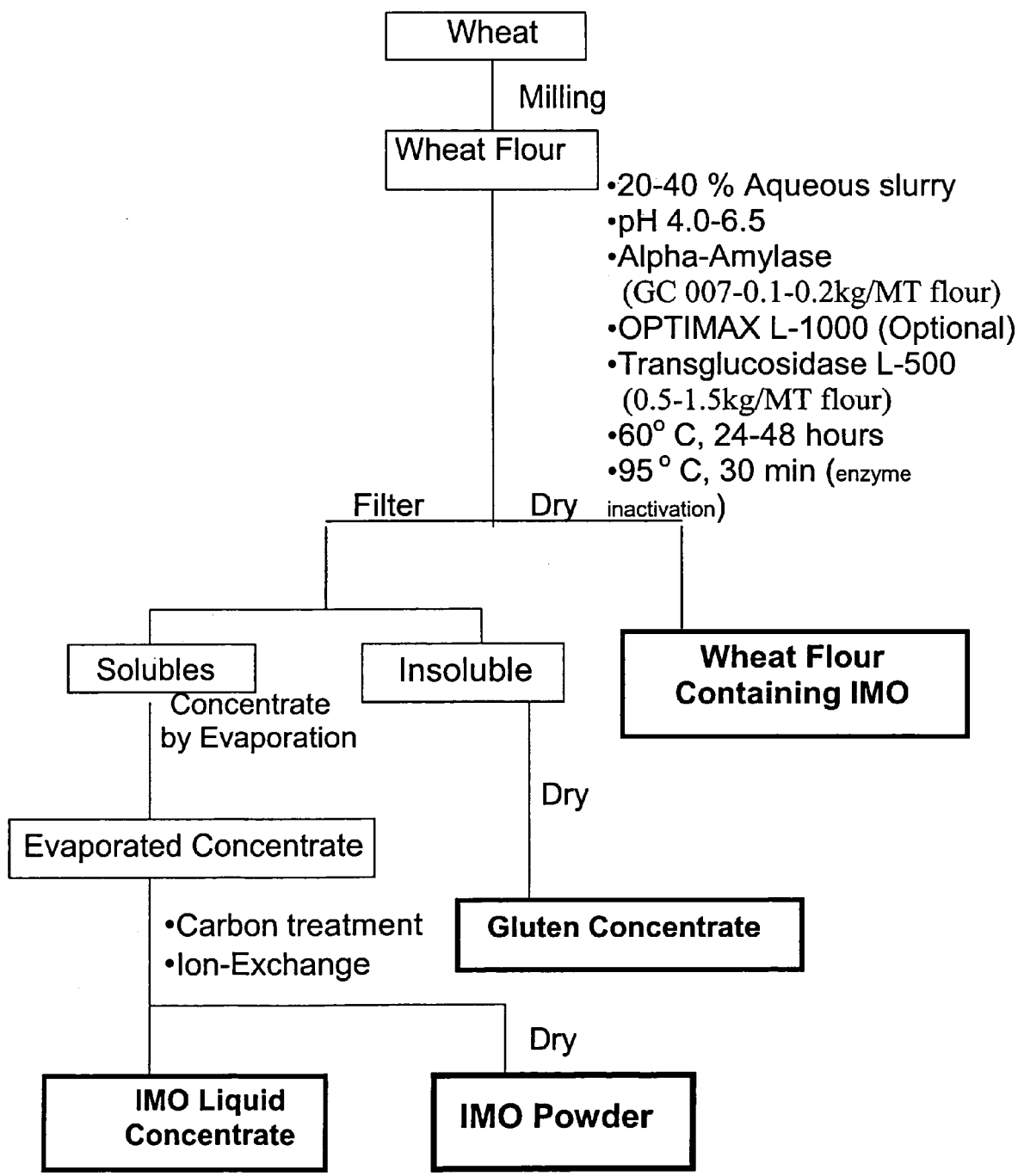
FIG. 2 is another flowchart describing the production of isomalto-oligosaccharide enriched wheat flour.

In another embodiment, the invention describes a method for making a wheat grain composition said method comprising: (a) contacting an ungelatinized wheat grain having an endogenous maltogenic beta-amylase and a starch liquefying alpha amylase from *Bacillus* to produce maltose; (b) contacting said maltose with a transglucosidase, wherein said steps (a) and step (b) occur at a temperature less than wheat gelatinizing temperature; and (c) obtaining a wheat grain composition having an enzymatically produced isomalto-oligosaccharide, wherein said oligosaccharide is derived from said ungelatinized grain. An embodiment of the present invention is depicted in FIG. 2.

In another embodiment, the above described method can be used to make a food additive, a bakery product, oral rehydration solution and/or a flour. In another embodiment, the maltogenic enzyme is a beta amylase. In another embodiment, the maltogenic enzyme is endogenous to the grain. In another embodiment, the starch liquefying enzyme is an alpha amylase derived from a bacterial source. In one embodiment the bacterial source is a *Bacillus* sp. In another embodiment, the starch liquefying enzyme is derived from *Bacillus licheniformis* or *Bacillus stearothermophilus*. In another embodiment, the transglucosidic enzyme is a transglucosidase. In another embodiment. The transglucosidase is derived from a fungal source. In one embodiment the fungal source is an *Aspergillus* sp. In another embodiment, the *Aspergillus* is *Aspergillus niger*. The invention also describes a grain composition, a food additive, oral rehydration solution and/or a flour produced according to above described method. The grain composition could contain greater than 1% by weight of at least one isomalto-oligosaccharide. The at least one isomalto-oligosaccharide can be selected from the group consisting of isomaltose, panose, isomalto-triose. In a further embodiment of the invention, the endogenous maltogenic enzyme is selected from beta amylase or alpha amylase. In a still further embodiment of the invention, the solubilizing enzyme is a liquefying alpha amylase derived from a *Bacillus*. In a still further embodiment of the invention the liquefying amylase is derived from *Bacillus licheniformis* or *Bacillus stearothermophilus*.

Substrates

The present invention includes a substrate containing a starch, for example a grain or a tuber containing a starch that is contacted with a maltogenic enzyme and a starch liquefying enzyme to produce maltose. The term substrate refers to materials that can be enzymatically converted to maltose and thus IMO's. Exemplary substrates can be at least one substrate selected from the group consisting of grains and tubers. The maltose can be in the form of a maltose rich syrup or slurry.

Starch occurs in two forms, amylose, a linear chain polysaccharide, and amylopectin, a branched chain polysaccharide. Amylose contains long unbranched chains in which all the D-glucose units are linked by alpha-1,4-linkages ("α-1,4 linkages" or "1,4-α-D-glucosyl linkages"). Amylopectin is highly branched, the backbone glucosidic linkage being α-1,4, but the branch points being α-1,6 linkages. The major components of starch can be enzymatically hydrolyzed in two different ways. Amylose can be hydrolyzed by α-amylases (E.C. 3.2.1.1), e.g., α-(1-4)-glucan 4-glucanohydrolase. Alpha amylases hydrolyze the α-(1,4)-linkages to yield a mixture of glucose, maltose, maltotriose and higher sugars. Amylose can also be hydrolyzed by a beta-amylase (E.C. 3.2.1.2) [alpha(1,4)-glucan maltohydrolase, 1,4-α-D-glucan maltohydrolase]. This enzyme cleaves away successive maltose units beginning from the non-reducing end to yield maltose quantitatively. The alpha and beta amylases also hydrolyze amylopectin. Neither the alpha and beta amylases can hydrolyze the alpha (1-6) linkages at the branch points of amylopectin. The end product of exhaustive beta-amylase action on amylopectin is a large, highly branched core or beta limit dextrin. A debranching enzyme (E.C. 3.2.1.41, e.g., pullulanases, [α-(1-6)-glucan 6-glucanohydrolase, also called α-(1,6)-glucosidase]) can hydrolyze the α-(1-6) linkages at the branch points. Thus the combined action of β-amylase and the α 1,6-glucosidase can therefore completely degrade amylopectin to maltose and glucose, resulting in a maltose content as high as 60%, 65%, 79%, 75%, 80% or higher of the total sugar content.

For the purposes of this invention, the substrate containing starch can be a grain or a tuber or mixtures thereof. The grain can be any cereal or seed containing starch. The substrate can be milled, ground or otherwise reduced in size to increase the surface area of the substrate for contacting with the respective enzymes. For example, the substrate can be wet or dry milled as desired. In one embodiment of the present invention, the starch is granular starch. Grains contemplated for use within the present invention includes any grain currently used in baking, pasta or other uses. Exemplary grains contemplated by the inventors include, but are not limited to at least one selected from the group consisting of wheat (*Triticum* sp. Including, but not limited to *T. monococcum, T. turgidum, T. spelta*, and/or *T. aestivum*), barley (e.g., *Hordeum vulgare*, and the varieties described in U.S. Pat. No. 6,492,576, Table 1), rye (*Secale* sp., including but not limited to *S. cereale*), corn (*Zea* sp., including, but not limited to *Zea mays*), buckwheat (*Fagopryum* sp., including, but not limited to *F. esculentum*), malt (for example, germinated barley), sorghum (*Sorghum* sp., including, but not limited to *Sorghum bicolor*) or otherwise known as milo, millet (ragi) (*Panicum* sp. and *Setaria* sp., including, but not limited to *P. milaceum*; and *Setaria* sp., including, but not limited to *S. italica*) and rice (*Oryza* sp., including, but not limited to *Oryza sativa*). It is contemplated by the inventors that wild-type and transgenic plants having beneficial attributes, such as increased enzyme levels of endogenous enzymes or the presence of exogenous enzymes are also useful as starch containing substrates.

Germinated cereals, for example, malt, are used as one of the key ingredients in many food and health drink formulations because of their high nutritive value, e.g., malt containing food products (TABLE A). Germination results in the synthesis and activation of endogenous maltogenic and proteolytic enzymes. Thus germinated cereals are a good source of grains containing endogenous maltogenic enzymes. Malt flour and malt extract are also used as a source of digestive enzymes in brewing and baking applications. However, germination of the barley renders the cereal grain components too readily digestible to play an effective role as a prebiotic or even as a nutraceuticals, since they tend to be digested in their entirety before arrival in the lower gastrointestinal tract. Unfortunately, the beneficial effects of prebiotic compounds are best realized in the lower gastrointestinal tract. Therefore, converting the highly digestible malto-sugars into less digestible isomalto sugars allows for the use of the modified malt to play a role as a prebiotic, allowing the malt to arrive in the lower gastrointestinal tract and provide additional functional and health benefits. For example, suitable commercially available food products containing malt extract are provided in Table A.

TABLE A

Commercial Food Products Containing Malt Extract

| Tradename | Manufacturer | Location |
|---|---|---|
| HORLICKS | Glaxosmithkline | Punjab, India |
| MALTOVA | Glaxosmithkline | Punjab, India |
| VIVA | Glaxosmithkline | Punjab, India |
| BOURNAVITA | Cadbury | Mumbai, India |
| BOOST | Jagjit Industries | Punjab, India |
| MILO | Nestle | New Delhi, India |

Thus the use of malt as a starch containing substrate converts some of the granular starch contained within the substrate to an additional beneficial form of the oligosaccharide, e.g., an IMO.

In addition, the substrate containing starch can be a tuber. Tubers contemplated by the inventors include potato (*Solanum* sp., including, but not limited to *S. tuberosum*), sweet potato (*Ipomoea* sp., including, but not limited to *Ipomoea batatas*), manioc [tapioca, cassaya] (*Manihot* sp., including, but not limited to *Manihot esculenta, Manihot aipi* and *Manihot utilissima*) and/or taro root (*Colocasia* sp., including, not limited to *C. esculenta* or *C. macrorhiza*).

The amount of substrate containing starch can be an aqueous slurry characterized by having a concentration of 10 to 50% dissolved solids (DS). In another embodiment, the substrate containing starch is characterized by having a concentration of 2-90% DS. In another embodiment, the substrate containing starch is characterized by having a concentration of 5-70% DS. In another embodiment, the substrate containing starch is characterized by having a concentration of 10-60% DS. In another embodiment, the substrate containing starch is characterized by having a concentration of 20-40% DS. In another embodiment, the substrate containing starch is characterized by having a concentration of 25-35% DS.

In another embodiment of the invention, the pH of the substrate containing starch is between 1.00 to 9.00. In another embodiment of the invention, the pH of the substrate containing starch is between 2.00 to 8.00. In another embodiment of the invention, the pH of the substrate containing starch is between 3.00 to 7.50. In another embodiment of the invention, the pH of the substrate containing starch is between 4.00 to 6.50. In another embodiment of the invention, the pH of the substrate containing starch is between 4.25 to 5.75.

Enzymes

The present invention includes contacting the substrate containing starch with a maltogenic and a starch liquefying enzyme to produce maltose. By maltogenic is meant that the enzyme is able to enzymatically convert starch to maltose. Exemplary maltogenic enzymes include alpha amylases and beta amylases. As described before, amylose can be hydrolyzed by αamylases (E.C. 3.2.1.1), e.g., α(1-4)-glucan 4-glucanohydrolase. Alpha amylases hydrolyze the α(1,4)-linkages to yield a mixture of glucose, maltose, maltotriose and higher sugars. Amylose can also be hydrolyzed by a beta-amylase (E.C. 3.2.1.2) [alpha(1,4)-glucan maltohydrolase, 1,4-α-D-glucan maltohydrolase]. This enzyme cleaves away successive maltose units beginning from the non-reducing end to yield maltose quantitatively. The alpha and beta amylases also hydrolyze amylopectin.

Alpha Amylases—

In some of the embodiments encompassed by the invention, the alpha amylase is a fungal or microbial enzyme having an E.C. number, E.C. 3.2.1.1-3 and in particular E.C. 3.2.1.1. In some embodiments, the alpha amylase is a thermostable fungal alpha amylase. Suitable alpha amylases may be naturally occurring as well as recombinant and mutant alpha amylases. In some embodiments, the alpha amylase is derived from a *Bacillus* species. Preferred *Bacillus* species include *Bacillus amyloliquefaciens, B. lentus, B. licheniformis*, and *B. stearothermophilus*. In particularly preferred embodiments, the alpha amylase is derived from a *Aspergillus* species. Preferred *Aspergilllus* species include *Aspergillus niger* and *Aspergillus oryzae*. Also reference is made to strains having NCIB 11837.

Commercially available alpha amylases contemplated for use in the methods of the invention include; CLARASE L ([*Aspergilus oryzae*] Genencor International Inc.) and NOVAMYL ([*B stearothermophilus*] Novozyme Biotech.).

As understood by those in the art, the quantity of alpha amylase used in the methods of the present invention will depend on the enzymatic activity of the alpha amylase. In general, an amount of about 0.01 to 5.0 kg of the alpha amylase is added to a metric ton (MT) of the substrate containing starch. Although in some embodiments the alpha amylase is added in an amount about 0.05 to 4.0 kg per MT. In other embodiments, the alpha amylase is added in an amount of about 0.1 to 2.5 kg per MT and also about 0.5 to 1.5 kg per MT. In further embodiments, other quantities are utilized. For example, generally an amount of between about 0.01 to 1.5 kg of CLARASE L (Genencor International Inc.) is added to a MT of starch. In other embodiments, the enzyme is added in an amount between about 0.05 to 1.0 kg; between about 0.1 to 0.6 kg; between about 0.2 to 0.6 kg and between about 0.4 to 0.6 kg of CLARASE L per MT of starch.

Beta Amylase

In some of the embodiments encompassed by the invention, the maltogenic enzyme is a beta amylase. While alpha amylases are maltogenic in the sense that contacting alpha amylases with a substrate containing starch would provide maltose, the use of beta amylases are useful in that their contact with granular starch would provide a greater amount of maltose to the exclusion of other saccharides, e.g., glucose. In some embodiments, the beta amylase is a plant or microbial enzyme having an E.C. number, E.C. 3.2.1.2 (for example those beta amylases described in U.S. Pat. Nos. 4,970,158 and 4,647,538). In some embodiments, the beta amylase is a thermostable bacterial beta amylase. Suitable beta amylases may be naturally occurring as well as recombinant and mutant beta amylases. The term bacterial refers to the enzyme being derived from *Bacillus* sp., e.g., *B. subtilis, B. licheniformis, B. stearothermophilus, B. coagulans, B.*

*amyloliquefaciens*, and/or *B. lentus*. Particularly preferred beta amylases are derived from *Bacillus* strains *B. stearothermophilus, B. amyloliquefaciens* and *B. licheniformis*. Also reference is made to strains having NCIB 11608. The term plant origin refers to the enzyme being derived, extracted, isolated, expressed from a plant source, for example from barley malt, soybean, wheat or barley.

Commercially available beta amylases contemplated for use in the methods of the invention include; OPTIMALT BBA, Spezyme DBA, and OPTIMALT ME (Genencor International Inc.). Other commercially available wheat beta amylases are also useful in the methods of the invention.

In some embodiments, the substrate containing starch, e.g., wheat, rye, barley, malt, comprises an endogenous maltogenic enzyme at sufficient levels to produce sufficient maltose for conversion to isomalto oligosaccharides. The term "endogenous" refers to the enzyme being present in the grain or tuber without having to resort to adding the maltogenic enzyme to the grain, or the grain being genetically engineered to provide maltogenic enzymes.

In embodiments where the substrate containing starch does not contain an endogenous maltogenic enzyme or has low endogenous levels of maltogenic enzymes, e.g., rice, millet, sorghum, and/or corn, the addition of an equivalent amount of any exogenous maltogenic enzyme is also contemplated by the inventors. The exogenous maltogenic enzyme can be added, for example by genetically manipulating the host cell to express sufficient levels of maltogenic enzyme, and/or providing a maltogenic enzyme concentrate or material from another source. The term exogenous maltogenic enzyme refers to a maltogenic enzyme that is not present within the grain. In this embodiment, a sufficient amount of maltogenic enzyme is contacted with the substrate to produce maltose.

In one embodiment, the amount of exogenous maltogenic enzyme contacted with the substrate containing starch is between 0.050 to 5.000 Degrees of Diastatic Power ("DP°") units/gm of maltogenic enzyme. In another embodiment of the invention, 0.100 to 2.000 DP° units/gm of maltogenic enzyme is contacted with the grain containing a starch. In still another embodiment of the invention, 0.100 to 3.000 DP° units/gm of maltogenic enzyme is contacted with the grain containing a starch.

In another embodiment, the amount of exogenous maltogenic enzyme contacted with the substrate containing starch is expressed in kilograms of maltogenic enzyme per metric ton of substrate. In one embodiment, the amount of exogenous maltogenic enzyme contacted with the substrate is about 0.05 kg of maltogenic enzyme per metric ton dry solids basis ("kg/mt dsb"). In another embodiment, the amount of exogenous maltogenic enzyme is about 0.1 kg of maltogenic enzyme per metric ton dry solids basis ("kg/mt dsb"). In other embodiments 0.2, 0.4, 0.6, 0.8. and/or 1.0 kg/mt dsb provide sufficient amounts of maltogenic enzyme, e.g., β-amylase.

In another embodiment, the amount of exogenous maltogenic enzyme contacted with the substrate containing starch is expressed in kilograms of maltogenic enzyme per metric ton of substrate. In one embodiment, the amount of exogenous maltogenic enzyme contacted with the substrate is about 0.05 kg of maltogenic enzyme per metric ton dissolved starch basis ("kg/mt dsb"). In another embodiment, the amount of exogenous maltogenic enzyme is about 0.1 kg of maltogenic enzyme per metric ton dissolved starch basis ("kg/mt dsb"). In other embodiments 0.2, 0.4, 0.6, 0.8. and/or 1.0 kg/mt dissolved starch basis provide sufficient amounts of maltogenic enzyme, e.g., β-amylase.

In another embodiment, the amount of maltogenic enzyme to be contacted with the grain is in terms of maltogenic enzyme units. Assays useful to determine the maltogenic activity include those described in the examples and those describing β-amylase activity. The term DP° unit refers to the amount of enzyme contained in 0.10 ml of a 5% solution of the sample enzyme preparation that will produce sufficient reducing sugars to reduce 5 ml of Fehling's solution when the sample is incubated with 100 ml of substrate for 1 hour at 20° C. (68° F.).

In another embodiment, a grain having endogenous maltogenic enzymes (barley, wheat, etc.) can be mixed with those grains needing exogenous maltogenic enzymes. Mixtures of 30:70, 60:40, 50:50, 60:40, 70:30 grains having an endogenous maltogenic enzyme: grains utilizing exogenous maltogenic enzyme sources are contemplated by the inventors, so long as sufficient amounts of maltogenic enzymes are present in the mixture (endogenous or exogenous sources). Use of endogenous sources of maltogenic enzymes can reduce the amount of exogenous enzymes added or contacted with the grain mixture.

Starch Liquefying Enzymes

A starch liquefying enzyme is contacted with the starch to reduce the viscosity of the liquefied or solubilized starch. In one embodiment of the invention the starch liquefying enzyme is an enzyme selected from the E.C. 3.2.1.1, e.g., alpha amylases. Exemplary alpha-amylases can be derived, isolated or extracted from a bacterial source. In one embodiment, the bacterial source is a *Bacillus*. In another embodiment, the alpha-amylases derived from *Bacillus* include those derived from at least one bacterial source selected from *B. subtilis, B. licheniformis, B. stearothermophilus, B. coagulans, B. amyloliquefaciens*, and *B. lentus*. Those of *Bacillus licheniformis* and *Bacillus stearothermophilus* are especially useful. Other amylases are contemplated by the inventors, for example, but not limited to those of EC 3.2.1.133 (U.S. Pat. No. 6,361,809). Other amylases contemplated by the inventors include those characterized by increased oxidative or thermostability, including those mutants or genetically modified or variant amylases described in U.S. Pat. Nos. 5,763,385; 5,824,532; 5,958,739; and/or 6,008,026. Useful alpha amylases are those derived from *B. licheniformis* strains NCIB 8059, ATCC 6598, ATCC 6634, ATCC 8480, ATCC 9945A, ATCC 11945. Useful alpha amylases are those derived from *B. stearothermophilus* strains ATCC 39709. Such enzymes are identified by the trade names "SPEZYME AA" or "SPEZYME FRED", "SPEZYME LT300", and "SPEZYME LT75", available from Genencor International (Palo Also, Calif., USA). Other such enzymes include alpha amylases from *Bacillus stearothermophilus* sold under the tradename GZYME G997, GC007 and from *Bacillus licheniformis* sold under the tradename GC262 SP, also available from Genencor International.

Contacting the grain containing starch with the maltogenic enzyme and the starch liquefying enzyme produces maltose. As understood by those in the art, the quantity of starch liquefying enzyme used in the methods of the present invention will depend on the enzymatic activity of the starch liquefying enzyme. In one embodiment, 0.01 to 25 Liquefon Units/gm of starch liquefying enzyme is contacted with the grain containing starch. In another embodiment, 1 to 10 Liquefon Units/gm of starch liquefying enzyme is contacted with the grain containing a starch. One Liquefon Unit (LU) is the measure of digestion time required to produce a color change with iodine solution, indicating a definite stage of dextrinization of starch substrate under specified conditions.

In one embodiment, 0.1 kg of starch liquefying enzyme is added per metric ton of grain dissolved solid basis (kg/mt dsb). In other embodiments, 0.2, 0.4, 0.4, 0.8, or 1.0 kg of starch liquefying enzyme is added per metric ton of grain (kg/mt dissolved starch basis). In one embodiment, 0.1 kg of starch liquefying enzyme is added per metric ton of grain dissolved starch basis (kg/mt dissolved starch basis). In other embodiments, 0.2, 0.4, 0.4, 0.8, or 1.0 kg of starch liquefying enzyme is added per metric ton of grain (kg/mt dissolved starch basis). Assays useful to determine the starch liquefying activity include those described in the examples herein. Exemplary assays for the determination of $\alpha$-amylase activity are also described in U.S. Pat. Nos. 5,763,385; 5,824,532; 5,958,739; and/or 6,008,026 which are incorporated by reference herein.

Transglucosidic Enzyme

Contacting the maltose with a transglucosidic enzyme obtains a grain composition having an enzymatically produced isomalto-oligosaccharide, derived from the grain containing starch. The transglucosidic enzyme catalyzes hydrolytic and transfer reactions on incubation with alpha-D-gluco-oligosaccharides to produce isomaltose, panose, kojibiose or nigerose. The presence of these sugars and thus conversion by the transglucosidic enzyme is indicated in an increased amount of DP2 disaccharides. The transglucosidic enzyme (E.C. 2.4.1.24) can be transglucosidase. Exemplary transglucosidase enzymes are identified as TRANSGLUCOSIDASE L-1000 (Genencor International, Inc.) and TRANSGLUCOSIDE L by Amano Enzymes, Inc., (Nagoya, Japan). In one embodiment the transglucosidic enzyme is derived from a filamentous fungal source, e.g., *Aspergillus* sp. The transglucosidic enzyme that is derived from *Aspergillus* can be derived from *Aspergillus niger*. In one embodiment, the *Aspergillus niger* strain is ATCC14916.

In this embodiment, a sufficient amount of the transglucosidic enzyme is contacted with the substrate, e.g. the grain containing a starch to produce maltose. As understood by those in the art, the quantity of transglucosidic enzyme used in the methods of the present invention will depend on the enzymatic activity of the alpha amylase. In one embodiment, 0.01 to 25.00 transglucosidase units ("TGU")/gm of transglucosidase is contacted with the grain containing a starch. In another embodiment of the invention, 0.05 TGU to 10.00 TGU/gm of transglucosidase is contacted with the grain containing a starch. In still another embodiment of the invention, 0.10 to 5.00 TGU/gm of grain is contacted with the grain containing a starch. The term TGU refers to the activity of the enzyme required to produce one micromole of panose per minute under the conditions of the assay.

In one embodiment, 0.05 to 6.00 kg of transglucosidic enzyme is added per metric ton of grain (kg/mt dsb). In another embodiment, 0.10 to 5.00 kg of transglucosidic enzyme is added per metric ton of grain (kg/mt dsb). In another embodiment, 0.25 to 3.00 kg of transglucosidic enzyme is added per metric ton of grain (kg/mt dsb). In another embodiment, 0.50 to 1.50 kg of transglucosidic enzyme is added per metric ton of grain (kg/mt dsb). Additional assays useful to determine the transglucosidic activity include those described in the Examples and in Shetty, J., et al (U.S. Pat. No. 4,575,487 (1986) entitled, "Method for determination of transglucosidase"), which are incorporated by reference herein.

In one embodiment, 0.05 to 6.00 kg of transglucosidic enzyme is added per metric ton of dissolved starch (kg/mt starch dsb). In another embodiment, 0.10 to 5.00 kg of transglucosidic enzyme is added per metric ton of grain (kg/mt starch dsb). In another embodiment, 0.25 to 3.00 kg of transglucosidic enzyme is added per metric ton of grain (kg/mt starch dsb). In another embodiment, 0.50 to 1.50 kg of transglucosidic enzyme is added per metric ton of grain (kg/mt starch dsb).

As a result of transglucosidase reactions, the malto-oligosaccharides are converted to isomalto-oligosaccharides resulting in a new class of polysaccharides containing higher proportion of glucosyl residues linked to a primary hydroxyl group of a glucose molecule from the non-reducing end. Isomalto-oligosaccharides produced by this method include isomaltose, panose, isomalto-triose, isomalto-tetrose, isomalto-pentose, isomalto-hexose and isomalto-heptose. These sugars are receiving increased attention as food additives because they help prevent dental caries (Oshima, et. al 1988, The caries inhibitory effects of gos-sugar in vitro and rat experiments. Microbial Immunol. 32.1093-1105)) and improve human intestinal microflora acting as a growth factor (prebiotic) for *bifidobacteria* (Komoto, et. al 1988; Effect of Isomalto-oligosaccharides on human fecal flora *Bifidobacteria* Micro flora 7, 61-69).

To ascertain the production of the IMO's, assays and/or other analytical methods can be used to determine the amount of IMO produced. One method for determining the levels of IMO produced includes high performance liquid chromatography (HPLC). For example, analysis of the mixture can provide an indication of the levels of the various sugars produced by the process. A useful rating is the degree of polymerization (DP) of the mixture. The term degree of polymerization is a measure of the relative amounts of the number of glucose residues in the molecule. For example, glucose (one glucosyl unit, the lowest level of polymerization) is usually found as DP1. Isomalto-oligosaccharides are usually found in DP2 (two glucosyl units). In one embodiment, the grain composition contains greater than at least 1%, at least 5%, at least 25%, at least 40%, at least 50%, at least 55%, at least 60%, at least 65%, at least 70% by weight of at least one isomalto-oligosaccharide. In one embodiment the at least one isomalto-oligosaccharide is selected from the group of isomaltose, panose and/or isomalto-triose. In one embodiment, the amount of isomalto-oligosaccharides produced in the grain composition is between 1% and 99% of the grain composition. In one embodiment, the amount of isomalto-oligosaccharides produced in the grain composition is between 1% and 90% of the grain composition. In one embodiment, the amount of isomalto-oligosaccharides produced in the grain composition is between 1% and 80% of the grain composition. In one embodiment, the amount of isomalto-oligosaccharides produced in the grain composition is between 1% and 70% of the grain composition. In one embodiment of the present invention, the total sugar present in the grain composition after the above described procedure includes a level of maltose in the total sugar content of greater than 50%, greater than 60%, greater than 70%, or greater than 80%. Levels of maltose greater than 50% include ranges from 50% to 85%, from 55% to 80%, and/or from 60% to 75%. The term RBS ratio refers to the ratio of maltose (DP2) present in the grain as compared to the level of maltotriose (DP3) present in the resultant grain composition. A higher RBS value indicates a higher amount of maltose present and thus a more complete conversion of the starch to maltose as opposed to the presence of other less desirable end-products, e.g., maltotriose. In one embodiment, the RBS ratio is greater than 2.0. In one embodiments, the RBS ratio is greater than 3.0, greater than 4.0. Exemplary ranges include an RBS ratio of 2.0 to 50.0, 2.0 to 30.0 and/or 2.0 to 10.0. Various RBS ratios are described in the examples. It is noted that the hydrolysis of liquefied starch by commercial beta-amylases (barley or wheat) generally produces a maltose content between 55% and 65%. For maltose content greater than 50% using liquefied starch, the addition of debranching enzyme and/or a very low starting DE of the liquefied starch was previously required. Optionally, the addition of a debranching enzyme can be used to increase the production of maltose. The term debranching enzyme refers to enzymes that catalyze the hydrolysis of α-1,6-linkages. An enzyme of the class E.C. 3.2.1.41 is useful in this regard. An exemplary enzyme of this class is a pullanase, also known as α-dextrin endo-1,6-α glucosidase, limit dextrinase, debranching enzyme, amylopectin 1,6-glucanohydrolase.

Contacting the grain containing starch with a maltogenic enzyme to produce the maltose and the contacting of the maltose with a transglucosidic enzyme occurs at a temperature less than the gelatinization temperature of the starch of the grain used. The enzymes are contacted or incubated with the respective enzymes for an incubation time of at least 12 hours, at least 18 hours, at least 24 hours, at least 30 hours and/or at least 36 hours. The period of at least a noted time refers to a period of 12-80 hours, at least 18-60 hours and/or at least 24-48 hours. The term incubation time refers to the period of time for the conversion of maltose or the substrate to IMO's. The transglucosidic enzyme can be contacted or added separately or concurrently with the substrate, e.g. grain containing starch, the maltogenic enzyme, e.g., the alpha amylase or beta amylase, and/or the liquefying enzyme, e.g., the alpha amylase. In one embodiment, the transglucosidic enzyme is added concurrently with the liquefying enzyme. Thus in one embodiment, steps (a) and (b) are performed concurrently. In another embodiment, the steps (a) and (b) are performed sequentially or separately. In another embodiment, the step (a) is performed before step (b). The term gelatinization temperature refers to the temperature at which the starch contained within the grain changes phases or gelatinizes. While the specific temperature varies from grain to grain, temperatures sufficient to effect the gelatinization of starch include those greater than 45° C., greater than 50° C., greater than 60° C., greater than 70° C., greater than 80° C., and/or greater than 90° C. Exemplary temperatures greater than the indicated gelatinization temperatures include 45° C. to 120° C., 50° C. to 110° C., 500 to 100° C. In one embodiment, e.g. wheat, the gelatinization temperature is a temperature the grain is kept below, e.g. a temperature selected from below 50° C. to 70° C., in another embodiment below 55° C. to 65° C., and in another embodiment, below 60° C. For example, gelatinization temperatures have been described for corn, potato, wheat, tapioca, waxy maize, sorghum, rice sago, arrowroot amylomaize and/or sweet potato as shown in Table 1 (Beynum, G. M. A and Roels, J. A., Starch Conversion Technology (Marcel Dekker, Inc., New York, N.Y. (1985), pp. 15-45):

TABLE 1

| Starch | Kofler gelatinization temperature range (° C.) | Brabender pasting temperature (° C.) |
|---|---|---|
| Corn | 62-67-72 | 75-80 |
| Potato | 58-63-68 | 60-65 |
| Wheat | 58-61-64 | 80-85 |
| Tapioca | 59-64-69 | 65-70 |
| Waxy Maize | 63-68-72 | 65-70 |
| Sorghum | 68-74-78 | 75-80 |
| Rice | 68-74-78 | 70-75 |
| Sago | 60-66-72 | 65-70 |
| Arrowroot | 62-66-70 | |
| Amylomaize | 67-80-92 | 90-95 |
| Sweet Potato | 58-65-72 | 65-70 |

In another embodiment of the present invention, the slurry, after the incubation time, can be subjected to a flash heat period sufficient to halt further enzymatic activity, but not gelatinize or liquefy the slurry. For example, the slurry can be heated to a temperature of 80°, 85°, 90° 95° or 100° C. for a period of 5-60 minutes, 10.0 to 40.0 minutes or 30.0 minutes.

Another embodiment of the present invention further includes the step of separating the slurry into insolubles and solubles. The separating step can be by any chromatographic method known in the arts, for example, but not limited to HPLC, size exclusion and/or charge chromatography. Filtering can be used to separate the insolubles from the solubles. The insolubles or entire slurry can be subjected to the drying steps described later in this application. In another embodiment, the solubles resulting from the separating step can be concentrated by evaporation, for example by roto-evaporation, tray drying, etc. The evaporated concentrate can be subjected to carbon treatment (filtered through carbon granules) and/or further chromatographic treatment to provide an isolated IMO liquid concentrate. The isolated IMO concentrate can have an IMO concentration of greater than 75%, greater than 85%, greater than 90%, greater than 95%, greater than 97%, and/or greater than 99%.

Another embodiment of the present invention is the use or incorporation of such syrup (the isomalto-oligosaccharides enzymatically derived from the substrate having ungelatinized starch) in oral rehydration solutions. The amount of the isomalto-saccharides can be in the amounts or formulations as described as U.S. Pat. Nos. 4,981,687; 5,096,894; and/or 5,733,579.

Another embodiment of the present invention is the drying of the aforementioned isomalto-oligosaccharide substrate, grain or tuber composition to produce a powder including the grain composition. Typically, this drying step is accelerated by heating. The grain composition can be dried to a desired moisture level by using a suitable drying method, for example, but not limited to a spray dryer, tray dryer, tumble dryer, drum dryer or cabinet dryer. Other drying methodologies can be used, for example spray drying, evaporative drying under reduced pressure.

By drying the grain composition, slurry, separated insolubles, and/or separated solubles, a flour or other dried powder is obtained therefrom. The resulting powder or flour can be incorporated into compositions in which the presence of isomalto-oligosaccharides is desired, for example in food stuffs (breakfast cereals, pastas), food additives and baked goods. The term food additive refers to the use of the isomalto-oligosaccharides as a sprinkle on material, as an ingredient for use in the manufacture of other foods, and/or a topical ingredient added to the food.

In another embodiment, the dried powder can be incorporated into food supplements. The incorporation of the dried powder into a food supplement can be provided in any acceptable supplement or form. The dietary supplements can be formulated for oral administration in a matrix as, for example but not limited to, drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The dietary supplement can also be formulated for oral administration as a solution or suspension in an aqueous liquid, as a liquid incorporated into a gel capsule or as any other convenient form for administration or for rectal administration, as a suppository, enema or other convenient form. The isomalto-oligosaccharide composition can also be provided as a controlled release system.

The dietary supplement formulation can also include any type of acceptable excipients, additives or vehicles. For example, but not by way of limitation, diluents or fillers, such as dextrates, dicalcium phosphate, calcium sulfate, lactose, cellulose, kaolin, mannitol, sodium chloride, dry starch, sorbitol, sucrose, inositol, powdered sugar, bentonitc, microcrystalline cellulose, or hydroxypropyl methylcellulose may be added to isomalto-oligosaccharide composition to increase the bulk of the composition. Also, binders, such as, but not limited to, starch, gelatin, sucrose, glucose, dextrose, molasses, lactose, acacia gum, sodium alginate, extract of Irish moss, panwar gum, ghatti gum, mucilage of isapgol husks, carboxymethylcellulose, methylcellulose, polyvinylpyrrolidonc, Veegurn and starch arabogalactan, polyethylene glycol, ethylcellulose, glycerylmonostearate and waxes, may be added to the formulation to increase its cohesive qualities.

Additionally, lubricants, such as, but not limited to, glyceryl monostearate, talc, magnesium15 stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the formulation. Also, glidants, such as but not limited to, colloidal silicon dioxide, magnesium silicate or talc may be added to improve the flow characteristics of a powdered formulation. Finally, disintegrants, for example, but not limited to, starches, clays, celluloses, algins, gums, crosslinked polymers (e.g., croscarmelose, crospovidone, and sodium starch glycolate), Veegum, methylcellulose, agar, benton:ite, cellulose and wood products, natural sponge, cation-exchange resins, alginic acid, guar gum, citrus pulp, carboxymethylcellulose, or sodium lauryl sulfate with starch may also be added to facilitate disintegration of the formulation in the stomach or intestine.

Another embodiment of the present invention is the use of the novel substrate, tuber or grain composition described herein in the production of flour for use in various baked goods. The term baked goods refers to leavened and unleavened goods. The term leavened refers to baked goods using yeast in the baking process. Whereas the term unleavened means baked goods not using yeast in the baking process. Exemplary goods include bread, cookies, cakes, pies, biscuits, naan, bagels, pasta, crackers, rolls, donuts, pitas and pastries. Exemplary unlevened goods include matzoh, chapathi, breakfast cereals and tortillas. Another embodiment of the present invention is the use of the novel grain compositions in pasta, for example, noodles (penne, spaghetti, lasagna, udon, etc.). Another embodiment of the present invention is a substrate, tuber or grain composition made according to the above-described method. Another embodiment of the present invention is a flour comprising the substrate, tuber or grain composition made according to the above described method. Another embodiment of the present invention is an oral rehydration solution comprising the isomalto-oligosaccharide described above. Flour comprising the substrate, tuber or grain composition can be made according to the above described method. Another embodiment of the present invention is a substrate, tuber or grain composition made according to the above-described method.

Another embodiment of the present invention is a substrate, tuber or grain composition made according to the above-described method. Another embodiment of the present invention is the use of the novel grain compositions in fermentive/beer worts or substrates. For example, the novel grain composition can be used as described in beer fermentation as described in International Publication No WO 02/20712 A1, which is incorporated by reference herein. The novel grain compositions can also be incorporated in beer adjuncts.

The isomalto-oligosaccharide containing substrate can also be subjected to an additional step of recovering the maltose by extraction and isolation of the generated maltose, for example as a maltose syrup. The syrup can be extracted and/or isolated from the grain composition by methods familiar in the art, for example in U.S. Pat. Nos. 3,922,196 and 4,113,509, which are incorporated by reference herein.

Another route to enhance the sweetness or the isomalto-oligosaccharide content, is to treat the produced isomalto-oligosaccharide syrup with a hydrolase (in soluble or immobilized form) which hydrolyses preferentially or even exclusively malto-oligosaccharides, and has only a small or even no affinity for isomalto-oligosaccharides. Examples of such an enzyme is glucoamylase from *A. niger* or other sources like *Aspergillus* sp. or *Rhizopus* sp. which preferentially hydrolyses malto-oligosaccharides (Manjunath P., Shenoy B. C., Raghavendra Rao M. R., Journal of Applied Biochemistry, 5(1983),235-260; Meagher M. M., et al., Biotechnology and Bioengineering, 34(1989), 681-693; Pazur J. H., Kleppe K., The Journal of Biological Chemistry, 237(4) (1962),1002-1006; Hiromi K., Nitta Y., et al., Biochimica et Biophysica Acta, 302(1973),362-37).

Also an enzyme like the alpha-D-glucopyranosidase from *Bacillus stearothermophilus* can be applied. This enzyme is not capable of hydrolysing isomalto-oligosaccharides and will only degrade the malto-oligosaccharides present in the isomalto-oligosaccharide rich syrup (Suzuki Y., Shinji M., Nobuyuki E., Biochimica et Biophysica Acta, 787(1984), 281-289). Also other alpha-D-glucosidases which are called maltases can be used. The maltase from yeast for example will only hydrolyse maltose and to a lesser extent maltotriose (Kelly C. T., Fogarty W. M., Process Biochemistry, May/June (1983),6-12).

After the hydrolysis of the malto-oligosaccharides to glucose, the syrup can be enriched in isomalto-oligosaccharides by a chromatographic technique or by nano- or ultra-filtration.

The following examples serve to illustrate the main embodiments of this invention.

EXAMPLES

The following specific examples further illustrate the compositions and the methods of the invention. It is to be understood that these examples are for illustrative purposes only and can be applied to any other suitable materials rich in starch and containing endogenous maltose producing enzyme, for example, wheat, rice, barley, malt, potato, sweet potato, etc.

Enzyme Activity Determination

The transglucosidase activity is measured by the method of Shetty, J., et al, 1986 (U.S. Pat. No. 4,575,487).

The beta amylase activity was measured by a 30-minute hydrolysis of a starch substrate at pH 4.6 and 20° C. The reducing sugar groups produced on hydrolysis are measured in titrimetric procedure using alkaline ferricyanide. One unit of diastase activity, expressed as degrees DP refers to the amount of enzyme, contained in 0.1 ml of 5% solution of the sample enzyme preparation that will produce sufficient reducing sugars to reduce 5 mL of Fehlings' solution when the sample is incubated with 100 mL of the substrate for 1 hour at 20 C.

The alpha amylase activity was developed based on an end-point assay kit supplied by Megazyme (Aust.) Pty. Ltd. A vial of substrate (p-nitrophenyl maltoheptaoside, BPNPG7) was dissolved in 10 ml of sterile water followed by a 1:4 dilution in assay buffer (50 mM maleate buffer, pH 6.7, 5 mM calcium chloride, 0.002% Tween20). Assays were performed by adding 10 μl of amylase to 790 μl of the substrate in a cuvette at 25° C. Rates of hydrolysis were measured as the rate of change of absorbance at 410 nm, after a delay of 75 seconds. The assay was linear up to rates of 0.2 absorption units/min.

α-Amylase protein concentration was measured using the standard Bio-Rad Assay (Bio-Rad Laboratories) based on the method of Bradford, *Anal. Biochem.*, Vol. 72, p. 248 (1976) using bovine serum albumin standards.

Substrates:

The wheat flour used as substrates in all examples, was purchased from retail commercial stores. Other tuber or grain substrates, e.g., rice and barley used as substrates may be purchased from commercial sources (Huai An Liujun Food processing company, Jiangsu province, China).

Oligosaccharide Analysis

The composition of the reaction products of oligosaccharides was measured by HPLC (Agilent 1010, Palo Alto, Calif., USA) equipped with a HPLC column (Rezex 8 u8% H, Monosaccharides), maintained at 60° C. fitted with a refractive index (RI) detector (ERC-7515A, RI Detector from The Anspec Company, Inc.). Dilute sulfuric acid (0.01 N) was used as the mobile phase at a flow rate of 0.6 ml per minute. Twenty microliter of 4.0% solution was injected on to the column. The column separates based on the molecular weight of the saccharides. For example a designation of DP1 is a monosaccharide, such as glucose; a designation of DP2 is a disaccharide, such as maltose; a designation of DP3 is a disaccharide, such as maltotriose and the designation DP4+ is an oligosaccharide having a degree of polymerization (DP) of 4 or greater. The term Higher sugar ("Hr. Sugar") refers to sugars having DP greater than 3.

For iso-saccharides or branched sugars, the reaction products were measured by HPLC (Agilent 1010, Palo Alto, Calif., USA) equipped with a HPLC column (Shodex Rspak Oligosaccharide Column #DC-613), maintained at 50° C. fitted with a refractive index (RI) detector (ERC-7515A, RI Detector from The Anspec Company, Inc.). 70 (Acetonitrile): 25 (methanol):5 Water was used as the mobile phase at a flow rate of 2.5 ml per minute. Twenty microliter of 4.0% solution was injected on to the column. The column separates based on the molecular weight of the saccharides. The standard sugars, glucose, maltose, maltotriose, isomaltose, panose and isomalto-triose (Sigma Chemicals, St. Louis, Mo., USA) were used to calibrate the column.

Example 1

Maltose production from wheat flour by alpha amylase from *Bacillus licheniformis* (an alpha amylase sold under the tradename GC262SP by Genencor International, Palo Alto, Calif.) and *Bacillus stearothermophilus* (an alpha amylase sold under the tradename GC007 by Genencor International, Palo Alto, Calif.) were compared. One hundred fifty grams of wheat flour from commercial retail sources was suspended in 450 ml of deionized water. The suspension was stirred for 15 minutes at room temperature for uniform mixing (pH 5.5). The pH was adjusted with 6.0 N sulphuric acid ($H_2SO_4$). The resultant suspension was kept in a water bath maintained at 60° C. and stirred for uniform mixing before the enzymes were added. About 6,000 LU/g of amylase from *Bacillus stearothermophilus* (0.6 kg of GC007 [from Genencor International. Inc.]/Metric ton (Mt) starch dsb) and 15,100 LU/g of amylase from *Bacillus licheniformis* (0.6 kg GC262 SP from [Genencor International. Inc.]/Mt. starch dsb) were added separately and incubated with constant stirring at 60° C. Samples were withdrawn at different predetermined intervals of time and analyzed for total sugar composition using high-pressure liquid chromatography (HPLC). Two ml of sample was taken from each container at a predetermined time interval using a plastic pipette and transferred to a centrifuge tube. The sample was centrifuged at 8000 prm for 3 minutes. The supernatent was withdrawn from the centrifuge tube and a few drops were placed into a sample well of a Lecia AR200 (Leica Microsystems, Inc., Buffalo, N.Y., USA) digital hand held refractometer and recorded (Table 2). The Brix (as a measure of the dissolved sugars) of the solution was determined (Table 2).

TABLE 2

Comparison of liquefying alpha amylases on the production of maltose during incubation of wheat flour at pH 5.5, 60° C.

| Enzyme & Dosage | Sugar & BRIX | Incubation Time, 1 hour at 60° Percent Sugar | | | After heating at 80° C., 30 minutes |
|---|---|---|---|---|---|
| | | 2 hours | 4 hours | 6 hours | |
| No added Alpha Amylase | DP1 | 3.86 | 3.70 | 3.74 | Gelatinized |
| | DP2 | 54.87 | 56.24 | 56.78 | |
| | DP3 | 2.83 | 3.44 | 3.96 | |
| | Hr. Sugar | 38.44 | 36.62 | 35.52 | |
| | BRIX | 11.00 | 12.70 | 14.10 | |
| B. Stearothermophilus | DP1 | 2.67 | 2.89 | 3.23 | 3.17 |
| | DP2 | 65.10 | 67.44 | 69.08 | 65.83 |

TABLE 2-continued

Comparison of liquefying alpha amylases on the production
of maltose during incubation of wheat flour at pH 5.5, 60° C.

| Enzyme & Dosage | Sugar & BRIX | Incubation Time, 1 hour at 60° Percent Sugar | | | After heating at 80° C., 30 minutes |
|---|---|---|---|---|---|
| | | 2 hours | 4 hours | 6 hours | |
| [GC007] 0.6 kg/MT starch .dsb | DP3 | 10.62 | 12.18 | 13.07 | 13.42 |
| | Hr. Sugar | 21.61 | 17.49 | 14.62 | 17.58 |
| | BRIX | 18.50 | 19.40 | 20.00 | 22.70 |
| B. licheniformis [GC262SP] 0.6 kg/MT starch .dsb | DP1 | 2.86 | 3.59 | 3.96 | 4.03 |
| | DP2 | 62.43 | 64.36 | 65.88 | 58.14 |
| | DP3 | 13.19 | 14.82 | 15.93 | 16.69 |
| | Hr. Sugar | 21.52 | 17.23 | 14.23 | 21.14 |
| | BRIX | 17.40 | 18.40 | 19.10 | 22.60 |

The results in Table 2 showed that wheat flour incubated with alpha amylase from *Bacillus stearothermophilus* gave a higher maltose content compared to the maltose content from the incubation with alpha amylase from *Bacillus licheniformis*. Incubation of wheat flour with alpha amylases resulted in a significant increase in the dissolved solids due to the hydrolysis of the granular starch compared to incubation of wheat flour without alpha amylase addition. It is interesting to note here that the reaction product of alpha amylase from *Bacillus stearothermophilus* resulted in a higher ratio of maltose to glucose and maltose to maltotriose compared to alpha amylase from *Bacillus licheniformis*. These results indicate that the alpha amylase from *Bacillus stearothermophilus* is an especially useful enzyme for producing very high maltose syrup.

Example 2

Effect of *Bacillus stearothermophilus* alpha amylase (alpha amylase sold under the tradename GC 007 by Genencor International, Palo Alto, Calif.) concentration on the maltose production during incubation with wheat flour. The experimental conditions were identical as explained in Example 1. In addition, *Bacillus stearothermophilus* (6,000 Units/g) was added at 0.1 Kg, 0.2 Kg and 0.6 Kg/MT of starch dsb. The results are summarized in table 3.

TABLE 3

Effect of Alpha Amylase [GC007] Concentration on Maltose
Yield during incubation of wheat flour, pH 5.5, 60° C.

| GC007 concentration | DP & BRIX | Incubation Time, 1 hour at 60° Percent Sugar | | | |
|---|---|---|---|---|---|
| | | 2 hours | 4 hours | 6 hours | 24 hours |
| 0.1 kg/MT starch.dsb | DP1 | 1.87 | 2.10 | 2.27 | 3.70 |
| | DP2 | 65.56 | 64.25 | 65.63 | 70.22 |
| | DP3 | 5.92 | 7.15 | 8.03 | 11.68 |
| | Hr. Sugar | 29.65 | 26.50 | 24.07 | 14.40 |
| | BRIX | 17.80 | 19.20 | 19.70 | 21.80 |
| 0.2 kg/MT starch.dsb | DP1 | 1.71 | 2.13 | 2.37 | 3.90 |
| | DP2 | 62.47 | 64.34 | 65.44 | 69.30 |
| | DP3 | 6.75 | 7.78 | 8.58 | 12.27 |
| | Hr. Sugar | 29.07 | 25.75 | 23.61 | 14.53 |
| | BRIX | 18.00 | 19.20 | 19.80 | 21.80 |
| 0.6 kg/MT starch .dsb | DP1 | 2.67 | 2.89 | 3.23 | 3.17 |
| | DP2 | 65.10 | 67.44 | 69.08 | 65.83 |
| | DP3 | 10.62 | 12.18 | 13.03 | 13.42 |
| | Hr. Sugar | 21.61 | 17.49 | 14.62 | 17.58 |
| | BRIX | 18.50 | 19.40 | 20.00 | 22.70 |

No significant effect of different levels of alpha amylase during the incubation of wheat flour was noticed either on the maltose content or on the dissolved solids. So, for further optimization studies, 0.1 Kg of GC007/MT. starch, dsb was used.

Example 3

One hundred fifty grams of wheat flour was suspended in 450 ml of deionized water and the pH was adjusted to pH 5.00, 4.50 and 4.00 using 6.0 N $H_2SO_4$. The slurry was stirred well for uniform mixing and the pH was adjusted until the specified pH was stabilized. GC007 was added at 0.1 Kgs/MT, starch dsb to each of the trial and incubated at 60° C. The samples were withdrawn at different predetermined intervals of time and the composition of the sugar and brix were measured as described in Example 1. (Table 4).

TABLE 4

Effect of pH on the maltose yield during incubation
of wheat flour with GC007

| PH | DP & BRIX | Incubation Time, 1 hour at 60° Percent Sugar | | | |
|---|---|---|---|---|---|
| | | 2 hours | 4 hours | 6 hours | 24 hours |
| 5.0 | DP1 | 2.59 | 3.22 | 3.77 | 5.17 |
| | DP2 | 63.87 | 66.89 | 67.41 | 65.77 |
| | DP3 | 10.90 | 13.23 | 14.25 | 16.87 |
| | Hr. Sugar | 22.64 | 16.66 | 14.57 | 12.19 |
| | BRIX | 17.70 | 18.80 | 19.20 | 20.90 |
| 4.5 | DP1 | 2.29 | 2.80 | 3.31 | 4.37 |
| | DP2 | 63.86 | 67.44 | 68.03 | 65.97 |
| | DP3 | 10.93 | 13.30 | 14.44 | 17.56 |
| | Hr. Sugar | 22.92 | 16.46 | 14.22 | 19.10 |
| | BRIX | 17.60 | 18.60 | 19.10 | 20.70 |
| 4.0 | DP1 | 1.71 | 1.79 | 2.11 | 3.17 |
| | DP2 | 58.19 | 60.23 | 61.28 | 62.95 |
| | DP3 | 11.16 | 13.47 | 14.87 | 18.67 |
| | Hr. Sugar | 28.93 | 24.51 | 21.74 | 15.21 |
| | BRIX | 17.60 | 18.60 | 19.00 | 19.50 |

The maltose content increased with decreasing pH of the incubation of the wheat flour from pH 5.5 and reached maximum of about 68% at pH 4.5 followed by a decrease at pH 4.0. This is an unexpected result showing the production of maltose content greater than 60% without the addition of a debranching enzyme during the hydrolysis of starch with plant beta amylases. The hydrolysis of liquefied starch by commercial Beta amylases (barley or wheat) generally produces maltose content between 55% and 60%. For maltose content greater than 60% using liquefied starch, the addition of debranching enzyme and or a very low starting DE of the liquefied starch are required. It is also important to note here that the process described in this invention allows maltose manufacturers to process at pH 4.5 and 60° C. that reduces the high risk of microbial contamination of the current process.

Example 4

One hundred fifty grams of wheat flour was suspended in 450 ml of deionized water and the pH of the slurry was adjusted to pH 4.5. The slurry was stirred well for uniform mixing and the pH was adjusted with 6.0 N $H_2SO_4$ until the pH was stabilized. The resultant suspension was kept in a water bath maintained at 60° C. and stirred for uniform mixing before the enzymes were added. A starch liquefying enzyme, e.g., a *Bacillus stearothermophilus* alpha amylase sold under the tradename "GC 007" (Genencor International, Inc.) was added at 0.1 Kg/MT, dsb. A debranching enzyme, a pullulanase sold under the tradename OPTIMAX L-1000 (Genencor International, Inc.) was then added at 0.25 Kg, 0.5 Kg and 1.0 Kg/M T dsb and incubated at 60° C. The samples were withdrawn at predetermined different intervals of time (2, 4, 6 and 24 hours) and the composition of the sugar and brix were measured as described in Example 1. The results were recorded (Table 5).

TABLE 5

Effect of debranching enzyme (OPTIMAX L-1000) on the maltose yield during incubation of wheat Flour with GC007 (0.1 Kg/MT, dsb) at pH 4.5, 60° C.

| OPTIMAX concentration | DP & BRIX | Incubation Time, 1 hour at 60° Percent Sugar | | | |
|---|---|---|---|---|---|
| | | 2 hours | 4 hours | 6 hours | 24 hours |
| 0.0 | DP1 | 1.21 | 1.38 | 1.47 | 1.99 |
| | DP2 | 62.77 | 64.69 | 66.24 | 67.16 |
| | DP3 | 6.29 | 7.32 | 8.64 | 10.97 |
| | Hr. Sugar | 29.73 | 26.61 | 23.65 | 19.90 |
| | BRIX | 17.5 | 18.6 | 19.4 | 20.40 |
| 0.25 Kg/MT dsb | DP1 | 1.28 | 1.33 | 1.90 | 1.94 |
| | DP2 | 66.61 | 69.97 | 72.01 | 73.64 |
| | DP3 | 8.18 | 10.03 | 10.68 | 13.58 |
| | Hr. Sugar | 23.93 | 18.67 | 15.41 | 10.86 |
| | BRIX | 17.70 | 18.60 | 19.40 | 20.80 |
| 0.50 Kg/MT dsb | DP1 | 1.41 | 1.41 | 1.64 | 2.01 |
| | DP2 | 70.50 | 73.35 | 74.46 | 74.32 |
| | DP3 | 9.62 | 11.26 | 11.94 | 14.31 |
| | Hr. Sugar | 18.47 | 13.98 | 11.96 | 9.36 |
| | BRIX | 17.70 | 18.70 | 19.80 | 20.80 |
| 1.00 Kg/MT dsb | DP1 | 1.47 | 1.56 | 1.58 | 2.02 |
| | DP2 | 72.90 | 75.54 | 76.08 | 75.21 |
| | DP3 | 10.05 | 11.35 | 11.95 | 13.53 |
| | Hr. Sugar | 15.48 | 11.55 | 10.39 | 9.24 |
| | BRIX | 17.60 | 18.80 | 19.70 | 21.70 |

Maltogenic enzymes (such as beta amylases) or starch liquefying alpha amylases (such as GC007) can not hydrolyze the alpha 1-6 glucosidic linkages, the branch point in the amylopectin of the starch substrate. So it is a common practice to add debranching enzyme, pullulanase (OPTIMAX L-1000 from Genencor International Inc) for producing maltose greater than 65% during the incubation of starch substrate with beta amylase. The effect of OPTIMAX L-1000 concentration during the incubation of wheat flour with GC007 was studied and the results were shown in Table 5. OPTIMAX L-1000 addition resulted in a significantly higher level (>75%) of maltose (DP2) compared to the control.

Example 5

It is generally the common practice in the industry to use high maltose syrup produced by an enzymatic process using a high temperature (>90° C.) enzyme liquefied starch substrate followed by treating with enzyme glucosyltransferase for producing isomalto-oligosaccharides syrups. This example illustrates the process of converting the granular starch in the wheat flour into isomalto-oligosaccharides in a single step. In this example, 275 grams of wheat flour was placed in a flask and 688 ml of deionized water was added. It was then stirred for 15 minutes for uniform mixing and the pH was then adjusted to pH 4.5 using 6.0 N $H_2SO_4$. The resultant suspension was kept in a water bath maintained at 60 C and stirred for uniform mixing before the enzymes were added. A starch liquefying enzyme, e.g., *Bacillus stearothermophilus* alpha amylase ([GC007 supplied by Genencor International] (0.1 Kgs/MT dsb) and a debranching enzyme, e.g., a pullulanase (OPTIMAX L-1000 supplied by Genencor International) (0.5 kgs/MT dsb) were added. The suspension was then divided into two equal parts. To one of the parts, an *Aspergillus niger* transglucosidase sold under the tradename "TRANSGLUCOSIDASE L-500" (Genencor International) was added at 1.0 Kg/MT dsb and kept in a water bath maintained at 60° C. (Sample 1). The other part was incubated first for four hours at 60°, followed by the addition of *Aspergillus niger* transglucosidase sold under the tradename "TRANSGLUCOSIDASE L-500" (Genencor International) at 1.0 Kg/MT dsb and maintenance in a water bath maintained at 60° C. (Sample 2).

The results shown in Table 6 indicate that conversion of the substrate to IMO's occurs with or without preincubation of the substrate (wheat flour) prior to the addition of the transglucosidase.

TABLE 6

Formation of isomalto-saccharides during the incubation of wheat flour with GC007 and OPTIMAX L-1000 at pH 4.5, 60° C., by TRANSGLUCOSIDASE L-500

| Sample | Reaction Time | Glucose | Maltose | Isomaltose | Maltotriose | Panose | Isomaltotriose | Branch G3+ | IMO No. |
|---|---|---|---|---|---|---|---|---|---|
| 1 | 17 | 14.74 | 30.27 | 2.73 | 6.82 | 23.05 | 7.13 | 14.65 | 47.56 |
| 2 | 17 | 13.92 | 33.17 | 2.32 | 7.70 | 23.69 | 4.88 | 14.32 | 45.21 |
| 1 | 48 | 16.90 | 20.04 | 7.98 | 10.29 | 22.35 | 3.95 | 17.95 | 52.23 |
| 2 | 48 | 14.96 | 23.59 | 6.85 | 12.17 | 16.65 | 5.57 | 19.66 | 48.73 |
| 1 | 72 | 16.78 | 21.21 | 5.78 | 8.51 | 22.83 | 4.17 | 20.24 | 53.02 |
| 2 | 72 | 15.24 | 25.44 | 4.99 | 8.88 | 18.48 | 7.52 | 19.03 | 50.01 |

IMO No. is calculated as the sum of isomaltose, panose, isomaltotriose and branched sugars greater than DP3

Incubation of modified wheat flour containing high content of maltose with Transglucosidase produced isomalto-oligosaccharides identical to the composition produced by the conventional process. The process is simple, economical and can be easily scaled to commercial production Example 6

It is common knowledge that cereals like wheat, barley and rye contain high levels of beta-amylase. Incubation of these cereals at 55°-60° C., pH 5.5 generally results in syrups containing greater than 50% maltose. A 28% slurry of wheat, barley and rye flour, respectively, was each prepared by adding 280 grams of the respective flour to 720 gm of deionized water. To each of these preparations, a *Bacillus stearothermophilus* alpha amylase (e.g., a *Bacillus stearothermophilus* alpha amylase sold under the trademark "GC007" by Genencor International) was added at 0.2 kg/MT of the flour. The pH was then adjusted to pH 5.5 using 6.0 N $H_2SO_4$ and incubated at 60° C. for 4.5 hours. The pH of the incubated samples was then adjusted to pH 4.5 using 6 N $H_2SO_4$ and 1.25 kg of transglulcosidase (e.g., a transglucosidase sold under the tradename TRANSGLUCOSIDASE L-500 by Genencor International)/MT of the flour was added. The slurries were then incubated at 60° C. water bath for 48 hours. The samples were then centrifuged and analyzed for IMO composition (Table 7) as set forth in Example 1.

TABLE 7

Soluble Carbohydrate Composition of Wheat, Barley and Rye After Incubating with GC007 and "TRANSGLUCOSIDASE L-500"

| Grains/Cereals | Treatment | Time (hours) | Soluble Carbohydrate Composition % | | | | | | | |
| --- | --- | --- | --- | --- | --- | --- | --- | --- | --- | --- |
| | | | Glucose | Maltose | Isomaltose | Maltotriose | Panose | Isomaltotriose | Branch G3+ | IMO No. |
| Wheat | Tg L-500* | 48 | 21.92 | 19.37 | 9.97 | 3.67 | 26.52 | 3.12 | 14.85 | 54.46 |
| Barley | Tg L-500* | 48 | 25.43 | 6.68 | 16.50 | 7.72 | 12.82 | 0.30 | 30.54 | 60.16 |
| Rye | Tg L-500* | 48 | 22.18 | 10.39 | 11.15 | 3.21 | 22.93 | 0.01 | 30.14 | 64.22 |

*Tg L-500 means "TRANSGLUCOSIDASE L-500"

Example 7

In an experiment, 140 grams of malt (Cargill Malt/Schreier-Malting Company, Wisconsin, USA) was mixed with 360 grams of distilled water. The slurry was stirred for 15.0 minutes at room temperature for uniform mixing and pH was then adjusted to pH 4.5 using dilute acetic acid. After stabilization of the pH, the slurry was kept in a water bath maintained at 60° C. Incubation was continued for 30.0 minutes with constant stirring and a 2 ml sample was withdrawn for Brix and HPLC analysis (0, time). Transglucosidase L-500 was added at 1.5 kg/MT malt and incubated at 60° C. Samples were withdrawn at different predetermined intervals of time during incubation, e.g., 2, 4, 6, 12, and 24 hours, to ascertain Brix and IMO composition (Table 8) as described in Example 1.

TABLE 8

Soluble Carbohydrate Composition of Malt After Incubating with TRANSGLUCOSIDASE L-500

| Grains/Cereals | Time (hours) | Brix | Soluble Carbohydrate Composition % | | | | | | | |
| --- | --- | --- | --- | --- | --- | --- | --- | --- | --- | --- |
| | | | Glucose | Maltose | Isomaltose | Maltotriose | Panose | Isomaltotriose | Branch G3+ | IMO No. |
| Malt | 0 | 15.70 | 16.42 | 33.87 | — | 14.04 | — | — | 35.66 | — |
| Malt | 2 | 16.50 | 19.59 | 21.91 | 0.75 | 7.70 | 9.38 | 2.87 | 31.40 | 44.40 |
| Malt | 4 | 16.70 | 21.82 | 19.70 | 0.90 | 6.16 | 12.35 | 1.42 | 30.94 | 45.62 |
| Malt | 6 | 16.90 | 24.43 | 18.29 | 1.00 | 4.63 | 11.50 | 2.51 | 30.73 | 45.84 |
| Malt | 12 | 17.00 | 28.37 | 15.74 | 3.93 | 4.32 | 8.36 | 2.68 | 29.10 | 43.98 |
| Malt | 24 | 17.00 | 33.24 | 14.94 | 5.96 | 2.34 | 5.50 | 3.34 | 26.15 | 40.95 |

The results in Table 8 showed that the commercial malt extract can be used as a suitable substrate for producing malt extract containing isomalto-oligosaccharides. The reaction time and the composition of IMO sugars of the malt extract could be adjusted by controlling the enzyme dosage. The addition of maltogenic enzymes can increase IMO content of the resulting composition.

Example 8

Sorghum, Millet and Rice (Exogenous Maltogenic Enzymes)

In another experiment, 280 grams of sorghum, millet and rice flour were each taken separately and mixed separately with 720 grams of deionized water.

The pH of the suspension was adjusted to pH 5.5 and a *Bacillus stearotherphilus* alpha amylase sold under the trademark "GC007" (Genencor International) was added at 0.5 kg/mt of the flour. After uniform mixing, the suspension was kept in a water bath maintained at 75° C. The reaction mixture was continuously stirred during incubation for 6 hours. The temperature was then reduced to 60° C. and a beta-amylase (sold under the tradename OPTIMALT BBA by Genencor International) was added at 1.0 kg/mt of the flour. The incubation was continued for additional 10-15 hours (a sample was taken for Brix and HPLC). After the specified time, the pH was reduced to pH 4.5 by 6N $H_2SO_4$ and an *Aspergillus niger* transglucosidase (sold under the tradename "TRANSGLUCOSIDASE L-500" by Genencor International) was added at 1.0 kg/mt flour. Samples were taken at 24 and 48 hrs. for analysis (Table 9).

TABLE 9

Soluble Carbohydrate Composition of Sorghum, Millet and Rice After "TRANSGLUCOSIDASE L-500" Treatment

| Grains/Cereals | Treatment | Time (hours) | Brix | Soluble Carbohydrate Composition % | | | | | Branch G3+ | IMO No. |
|---|---|---|---|---|---|---|---|---|---|---|
| | | | | Glucose | Maltose | Isomaltose | Maltotriose | Panose | Isomaltotriose | |
| Sorghum | Tg L-500* | 24 | 20.20 | 18.70 | 23.50 | 0.60 | 5.00 | 15.90 | 0.00 | 35.70 | 52.20 |
| | | 48 | 21.40 | 19.17 | 22.45 | 0.66 | 4.56 | 16.34 | 0.29 | 36.01 | 53.03 |
| Millet | Tg L-500* | 24 | 23.50 | 38.00 | 16.40 | 5.00 | 1.70 | 8.30 | 2.50 | 28.0 | 43.90 |
| | | 48 | 23.9 | 40.20 | 17.13 | 5.36 | 0.14 | 6.08 | 5.49 | 24.26 | 41.19 |
| Rice | Tg L-500* | 24 | 25.50 | 15.90 | 22.90 | 0.60 | 6.80 | 18.90 | 1.70 | 33.20 | 54.40 |
| | | 48 | 26.00 | 17.83 | 20.30 | 0.54 | 4.58 | 22.13 | 0.38 | 34.21 | 51.25 |

As shown in Table 9, IMO Numbers of 41 to 54% (52.20, 53.03, 43.90, 41.19, 54.40, and 51.25) were achieved.

Example 9

Mixed Grain/Cereals Composition

The data in Example 5 for wheat and Example 6 for barley and rye showed considerable amount of endogeneous maltogenic enzyme activity resulting in a syrup containing very high maltose. On the other hand, grains known to not contain endogenous maltogenic enzymes, for example sorghum, millet and rice, required the addition of exogenous maltogenic enzyme for producing the substrate suitable for transglucosidase treatment. In this experiment we studied the supplementation of maltogenic enzyme containing cereals like wheat or barley with sorghum and rice for converting the starch to substrates containing high maltose levels. In a typical experiment, a 15% suspension of sorghum and rice was prepared by suspending 140 grams of the flour in 720 grams of deionized water. The pH was adjusted to pH 5.5 using 6 N $H_2SO_4$ and *Bacillus stearothermophilus* alpha amylase sold under the trademark "GC007" (Genencor International) was added at 0.5 kg/mt of the flour. The resultant suspension was then left in a water bath maintained at 75° C. The suspension was stirred continuously for 6 hours. The temperature was then reduced to 60° C. Solid content of flour, e.g., pre-treated rice flour, was increased from 15% to 30% by the addition of barley flour. Similarly, wheat was added to pre-treated sorghum to a final concentration to reach 30%. The incubation was then continued for an additional 10-12 hrs. at 60° C. The pH was reduced to 4.5 and TRANSGLUCOSIDASE L-500 was added at 1.0 kg/mt flour. The incubation at 60° C. was continued for 24 hours and 48 hours. The samples were taken for HPLC analysis and brix; the results are shown in Table 10.

TABLE 10

| | | | Soluble Carbohydrate Composition of Millet and Barley; and Rice and Wheat | | | | | | |
|---|---|---|---|---|---|---|---|---|---|
| Grains/Cereals | Time (hours) | Brix | IMO No | Glucose | Maltose | Isomaltose | Panose | Maltotriose | Isomaltotriose | Branch G3+ |
| Wheat & | 24 | 16.1 | 48.70 | 29.50 | 18.60 | 2.90 | 1.00 | 13.00 | 3.40 | 29.50 |
| Sorghum (50:50) | 48 | 16.5 | 45.27 | 34.68 | 17.09 | 5.03 | 0.51 | 6.20 | 6.42 | 27.63 |
| Rice & Barley | 24 | 21.00 | 51.00 | 19.50 | 18.40 | 1.00 | 4.20 | 20.20 | 1.10 | 34.7 |
| (50:50) | 48 | 21.4 | 56.20 | 21.60 | 18.21 | 1.3 | 2.92 | 17.96 | 2.08 | 37.86 |

As shown in Table 10 above, the mixtures of millet and barley; and rice and wheat resulted in 45 to 56% IMO in the resultant suspension after the above described incubation periods.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A method for making an isomalto-oligosaccharide grain composition said method comprising:
   (a) contacting an ungelatinized starch in grain (insoluble starch) with an exogenous maltogenic enzyme and a starch liquefying enzyme to produce maltose;
   (b) contacting said maltose with a transglucosidic enzyme, wherein said steps (a) and (b) occur at a temperature less than or at the gelatinization temperature of said starch; and
   (c) obtaining a grain composition having an enzymatically produced isomalto-oligosaccharide, wherein said oligosaccharide is obtained from said grain.

2. The method according to claim 1, wherein said steps (a) and (b) occur concurrently.

3. The method according to claim 1, further comprising the step of drying said isomalto-oligosaccharide with or without separating insoluble solids.

4. The method according to claim 1, wherein said grain is selected from the group consisting of wheat, rye, barley, and malt.

5. The method according to claim 1, wherein said grain is selected from the group consisting of millet, sorghum and rice.

6. The method according to claim 1, wherein said maltogenic enzyme is a beta amylase.

7. The method of claim 6, wherein said beta amylase is obtained from a fungal, bacterial, or plant source.

8. The method of claim 6, wherein said beta amylase is obtained from a *Bacillus* species.

9. The method of claim 8, wherein said *Bacillus* species is selected from *Bacillus stearothermophilus*, *Bacillus amyloliquefaciens*, and *Bacillus licheniformis*.

10. The method of claim 6, wherein said beta amylase is obtained from a plant source selected from soybean, wheat, and barley.

11. The method according to claim 1, wherein said starch liquefying enzyme is an alpha amylase obtained from a *Bacillus* species.

12. The method according to claim 11, wherein said *Bacillus* species is *Bacillus licheniformis* or *Bacillus stearothermophilus*.

13. The method according to claim 1, wherein said transglucosidic enzyme is a transglucosidase.

14. The method according to claim 13, wherein said transglucosidase is obtained from an *Aspergillus* species.

15. The method according to claim 14, wherein said *Aspergillus* species is *Aspergillus niger*.

16. The method according to claim 1, wherein said isomalto-oligosaccharide is further purified.

17. The method of claim 1, wherein said isomalto-oligosaccharide is used as a food additive.

18. The method of claim 1, wherein said isomalto-oligosaccharide is used in a flour composition.

19. The method of claim 1, wherein said isomalto-oligosaccharide is used in an oral rehydration solution.

20. The method of claim 1, wherein said temperature less than or at the starch gelatinization temperature is below 50° C. to 70° C.

21. The method of claim 1, wherein said temperature less than or at the starch gelatinization temperature is below 55° C. to 65° C.

22. The method of claim 1, wherein said temperature less than or at the starch gelatinization temperature is below 60° C.

23. The method of claim 1, wherein step (a) further comprises contacting said ungelatinized starch with a debranching enzyme.

24. The method of claim 23, wherein said debranching enzyme is a pullulanase enzyme.

\* \* \* \* \*